United States Patent
Sarshar

(10) Patent No.: US 7,589,239 B2
(45) Date of Patent: Sep. 15, 2009

(54) THERAPEUTIC AGENTS FOR THE TREATMENT OF CANCER, METABOLIC DISEASES AND SKIN DISORDERS

(75) Inventor: Sepehr Sarshar, Cardiff by the Sea, CA (US)

(73) Assignee: Auspex Pharmaceuticals, Vista, CA (US)

( * ) Notice: Subject to any disclaimer, the term of this patent is extended or adjusted under 35 U.S.C. 154(b) by 0 days.

(21) Appl. No.: 12/064,552

(22) PCT Filed: Aug. 31, 2006

(86) PCT No.: PCT/US2006/034380

§ 371 (c)(1),
(2), (4) Date: Feb. 22, 2008

(87) PCT Pub. No.: WO2007/028104

PCT Pub. Date: Mar. 8, 2007

(65) Prior Publication Data

US 2008/0221069 A1    Sep. 11, 2008

Related U.S. Application Data

(60) Provisional application No. 60/713,822, filed on Sep. 2, 2005.

(51) Int. Cl.
A61K 31/69 (2006.01)
C07D 305/00 (2006.01)
C07F 5/02 (2006.01)

(52) U.S. Cl. .................. 568/1; 562/7; 514/64
(58) Field of Classification Search .............. None
See application file for complete search history.

(56) References Cited

U.S. PATENT DOCUMENTS

| | | |
|---|---|---|
| 4,717,720 A | 1/1988 | Shroot |
| 4,940,696 A | 7/1990 | Shroot |
| 5,098,895 A | 3/1992 | Shroot |
| 5,183,889 A | 2/1993 | Shroot |
| 5,212,303 A | 5/1993 | Shroot |
| 5,714,520 A | 2/1998 | Jones |
| 5,731,355 A | 3/1998 | Jones |
| 5,731,356 A | 3/1998 | Jones |
| 5,780,676 A | 7/1998 | Boehm |
| 5,908,869 A | 6/1999 | Jones |
| 5,952,382 A | 9/1999 | Bernardon |
| 6,204,257 B1 | 3/2001 | Stella |
| 6,254,853 B1 | 7/2001 | Hendler |
| 6,362,234 B1 | 3/2002 | Hendler |
| 7,250,412 B2 | 7/2007 | Marappan |
| 2001/0025035 A1 | 9/2001 | Stella |
| 2004/0053889 A1 | 3/2004 | Ebdrup |
| 2006/0041011 A1 | 2/2006 | Xu |
| 2007/0708189 | 4/2007 | Sarshar |
| 2007/0129392 A1 | 6/2007 | Hong |
| 2008/0234229 A1 | 9/2008 | Sarshar |
| 2008/0248093 A1 | 10/2008 | Marappan |

FOREIGN PATENT DOCUMENTS

| | | |
|---|---|---|
| WO | 9115464 A1 | 10/1991 |
| WO | 03057153 A2 | 7/2003 |
| WO | 2005000233 A2 | 1/2005 |
| WO | 2005044201 A2 | 5/2005 |
| WO | 2005108338 A1 | 11/2005 |
| WO | 2007022437 A2 | 2/2007 |
| WO | 2007028104 A2 | 3/2007 |

OTHER PUBLICATIONS

CAPLUS abstreact JP 2004018510 published on Jan. 22, 2004.*
Inoue et al. CAPLUS abstract of JP 2004018510, Pub. Date Jan. 22, 2004.*
Farol, L.T. et. al; Bexarotene: a clinical review; Expert Rev. Anticancer Ther., 2004, 4(2), 180-188.
Winum, J.-Y. et. al.; Synthesis of new targretin analogues that induce apoptosis in leukemia HL-60 cells; Bioorganic & Medicinal Chemistry Letters, 2002, 12, 3529-3532.
Dawson, M.I. et. al.; sp2-Bridged diaryl retinoids: effects of bridge-region substitution on retinoid X receptor (RXR) selectivity; Bioorganic & Medicinal Chemistry Letters, 2000, 10, 1307-1310.

(Continued)

Primary Examiner—Paul A Zucker
Assistant Examiner—Yevegeny Valenrod
(74) Attorney, Agent, or Firm—Dennis A. Bennett; Michael Sertic

(57) ABSTRACT

The present invention is directed to novel compounds according to formula (I) wherein $R_1$, $R_2$, and X are as defined herein. The invention also discloses methods of preparation, pharmaceutical compositions, and methods of disease treatment utilizing pharmaceutical compositions comprising these compounds. The compounds of this invention are novel therapeutic agents for the treatment of cancer, diabetes, metabolic diseases and skin disorders in mammalian subjects. These compounds are also useful modulators of gene expression. They exert their activity by interfering with certain cellular signal transduction cascades. The compounds of the invention are thus also useful for regulating cell differentiation and cell cycle processes that are controlled or regulated by various hormones or cytokines. The invention also discloses pharmaceutical compositions and methods of treatment of disease in mammals.

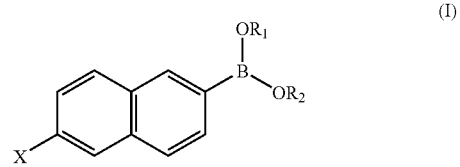

(I)

5 Claims, No Drawings

OTHER PUBLICATIONS

Yu, K.-L. et. al.; Application of the Heck reaction in the synthesis of truncated naphthoic acid retinoids; Bioorganic and Medicinal Chemistry Letters, 1996, 6(23), 2859-2864.

Dawson, M.I. et. al.; 4-[3-(5,6,7,8-tetrahydro, 5,5,8,8-tetramethyl-2-naphthalenyl)phenyl]benzoic acid and heterocyclic -bridged analogues are novel retinoic acid receptor subtype and retinoid X receptor a agonists; Bioorganic & Medicinal Chemistry Letters, 2000, 10, 1311-1313.

Jaeger, E.P. et. al.; Structure-activity relationship studies of retinoid cancer inhibition; Eur. J. Med. Chem., 1993, 28, 275-290.

Dawson, M.I. et. al.; Effect of structural modifications in the C7-C11 region of the retinoid skeleton on biological activity in a series of aromatic retinoids; J.Med. Chem., 1989, 32, 1504-1517.

Boehm, M.F. et. al.; Synthesis and Structure-activity relationships of novel retinoid X receptor-selective retinoids; J Med Chem, 1994, 37, 2930-2941.

Boehm, M.F. et. al.; Design and synthesis of potent retinoid X receptor slective ligands that induce apoptosis in leukemia cells; J Med Chem, 1995, 38, 3146-3155.

Dawson, M.I. et. al; Conformational effects on retinoid receptor selectivity. 2. Effects of retinoid bridging group on retinoid X receptor activity and selectivity; J Med Chem, 1995, 38, 3368-3383.

Koch, S.S.C. et. al.; Synthesis of retinoid X receptor-specific ligands that are potent inducers of adipogenesis in 3T3-L1 cells; J Med Chem, 1999, 42, 742-750.

Faul, M.M. et. al.; Synthesis of novel retinoid X receptor-selective retinoids; J Org Chem, 2001, 66, 5772-5782.

Banaszczyk, M.G. et. al.; Propofol Phosphate, a Water-Soluble Propofol Prodrug: In Vivo Evaluation; Anesth Analg, 2002, 95, 1285-92.

Fechner, J. et. al.; Pharmacokinetics and clinical pharmacodynamics of the new propofol prodrug GPI 15715 in volunteers; Anesthesiology, 2003, 99, 303-313.

Lee, J. et. al.; Phenolic modification as an approach to improve the pharmacology of the 3-acyloxy-2benzylpropyl homovanillic amides and thioureas, a promising class of vanilloid receptor agonists and analgesics; Bioorganic & Medicinal Chemistry, 2002, 10, 1171-1179.

Sliskovic, D.R. et. al.; Inhibitors of acyl-CoA: cholesterol O-acyl transferase (ACAT) as hypocholesterolemic agents. The synthesis and biological activity of a series of malonester amides; Bioorganic and Medicinal Chemistry Letters, 1996, 6(6), 713-718.

Lee, H.T. et. al.; Inhibitors of acyl-CoA: cholesterol O-acyl transferase (ACAT) as hypocholesterolemic agents: synthesis and structure-activity relationships of novel series of sulfonamides, acylphosphonamides and acylphosphoramidates; Bioorganic and Medicinal Chemistry Letters, 1998, 8, 289-294.

Langley, M.S. et. al.; Propofol: a review of its pharmacodynamic and pharmacokinetic properties and use as an intravenous anaesthetic; Drugs, 1988, 35, 334-372.

Bryson, H.M. et. al.; Propofol: an update of its use in anaesthesia and conscious sedation; Drugs, 1995, 50(3), 513-559.

Schywalsky, M. et. al.; Pharmacokinetics and pharmacodynamics of the new propofol prodrug GPI 15715 in rats; Eur J Anaesth, 2003, 20, 182-190.

Trapani, G. et. al.; Water-soluble salts of the aminoacid esters of the anaesthetic agent propofol; Int J of Pharma., 1998, 175, 195-204.

Charpentier, B. et. al.; Synthesis, structure—affinity relationships, and biological activities of ligands binding to retinoic acid receptor subtypes; JMC__1995__4993.

* cited by examiner

THERAPEUTIC AGENTS FOR THE TREATMENT OF CANCER, METABOLIC DISEASES AND SKIN DISORDERS

FIELD OF THE INVENTION

This invention is directed to novel therapeutic agents for the treatment of cancer, metabolic diseases and skin disorders in mammalian subjects.

Formula 1

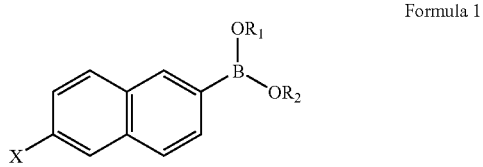

BACKGROUND OF THE INVENTION

Retinoids, natural and synthetic analogues of vitamin A, play a major role in controlling cell proliferation, differentiation, embryonic development and apoptosis. All-trans-Retinoic acid (ATRA), 13-cis-retinoic acid, and synthetic analogues are widely used for topical and oral administration in the management of dermatological diseases such as acne, psoriasis, and other disorders in which abnormal patterns of keratinization are found. Many biological effects of retinoids are mediated by the activation of a family of gene transcription factors known as Retinoic Acid Receptors (RARs) and Retinoid X Receptors (RXRs). Each class is composed of three distinct receptor subtypes ($\alpha$, $\beta$ and $\gamma$). After complexation with a ligand, RARs exert their gene transcriptional activity by forming a heterodimer with Retinoid X Receptors (RXRs). Side effects such as mucocutaneous irritation, hypervitaminosis A, and teratogenicity are drawbacks in the therapeutic use of retinoids.

The discovery of RAR and RXR subtypes has stimulated medicinal chemists to seek novel subtype-selective drugs with improved therapeutic indices. In normal skin, RAR-$\alpha$ and predominantly RAR-$\gamma$ are present in the keratinocytes of the epidermis. RAR-$\beta$ is neither expressed nor induced in this skin layer. In contrast, in the dermis, the fibroblast does express RAR-$\beta$ and in addition the gene encoding RAR-$\beta$ is also inducible by retinoic acid in this cell type. Consequently, in the field of dermatology, selective compounds for the RAR-$\gamma$ subtype act preferentially in the epidermis, while RAR-$\beta$ mediated action leads to response in fibroblasts; therefore, for skin disorders that involve the RAR signaling pathway, molecules with mixed RAR-$\beta$/$\gamma$ profiles are preferred.

Cancer is a complex disease characterized by genetic mutations that lead to uncontrolled cell growth. Cancerous cells are present in all organisms and under normal circumstances their excessive growth is tightly regulated by various physiological factors. One such regulatory process is apoptosis or programmed cell death. When the internal machinery of a cell detects abnormalities in cell division and growth, a signal is propagated within the cell, activating suicide proteins that kill the afflicted cell and prevent its proliferation. Such an apoptotic signal can be triggered, for example, when a ligand or drug interacts with a receptor or protein in the cell.

Most agents that induce apoptosis in cancer cells (e.g. Doxorubicin and Vincristine) are extremely toxic and cause a number of undesirable side effects. The toxicity associated with these therapies is a result of the non-specific interaction of the drug with the DNA of non-cancerous cells (e.g. intestinal and red blood cells). In order to circumvent such undesirable side effects, more selective compounds have been designed that inhibit one or more signaling proteins, growth factors and/or receptors involved in cancer cell proliferation. Examples include monoclonal antibodies for breast cancer (e.g. Herceptin) and Non-Hodgkin's Lymphoma (e.g. Rituxan), as well anti-angiogenic drugs for chronic myeloid leukemia (e.g. Gleevec). Since patient populations are genetically heterogeneous, it follows that a single selective therapy will not work in all cases, and as a result, cancer drugs are often used in combination. As such, there is a continual need for improved treatments.

Clinical studies have shown that retinoic acid and its synthetic analogs can inhibit the growth and invasion of cancer cells, and induce them to undergo apoptosis, thereby eradicating various types of cancers.

The novel compounds of this invention modulate the activity of Nuclear Retinoid receptors. These novel compounds are thus useful for regulating cell differentiation and cell cycle processes as well as other cellular signaling processes controlled or regulated by hormones and vitamins such as the thyroid hormone, vitamin D, all-trans retinoic acid and 9-cis-retinoic acid. Hence, conditions and/or diseases that are regulated by the aforementioned entities may be treated using the compounds of this invention. Examples of such conditions include for example cancer, mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia, acne, psoriasis, aging, wrinkling, diabetes, hyperglycemia, bone calcification, thyroid conditions, and the like.

Compounds that modulate the activity of RAR receptors are structural analogs of all-trans-retinoic acid. On the other hand compounds that modulate the activity of RXR receptors are structural analogs of 9-cis-retinoic acid (e.g. Bexarotene). The aforementioned modulators of Nuclear Retinoid receptors bear a carboxylic acid group in a specific position of the molecule. This acidic group forms a salt bridge to a basic residue in the binding pocket of the Nuclear Retinoid receptors. Research in this field indicates that removal of this acidic group drastically reduces the potency or the modulator. There are however, other amino acid residues in the binding pocket that can interact with the modulator. None of the modulators of Nuclear Retinoid receptors described to date take advantage of these critical interactions.

Another drawback of the current state of the art is the limited aqueous solubility of the selective Nuclear Retinoid receptor modulators. Said modulators mimic the structures of retinoic acids in order to conform to the three-dimensional structure and the hydrophobic nature of the respective binding pockets. In general, introduction of solubilizing substituents has resulted in lower in vitro binding affinity or increased in vivo metabolism and toxicity.

For treatment of skin disorders such as acne and psoriasis, agents are needed that can help alleviate the symptoms of the disorders without irritating the skin. Another drawback of the current state of the art is the low pKa of the carboxylic acid residue present in the selective Nuclear Retinoid receptor modulators. When applied topically, this acidic residue can lower the pH of the skin and in turn cause redness and irritation of the dermis.

Another major drawback of the current state of the art is the teratogenicity of currently prescribed retinoid acne medicines such as Differin® and Accutane®. In addition, Accutane® has also been associated with an increased risk of suicidal thoughts or actions (FDA Isotretinoin patient information sheet, August 2005). Studies have shown that certain modifications of the all-trans-retinoic acid backbone, specifically the carboxylic acid functional group, can produce non-teratogenic retinoid analogs that retain their pharmacological activity (Willhite et al *Toxicology and Applied Pharmacology* 1984, 74, 397-410; Willhite et al *Journal of National Cancer Institute* 1984, 72, 689-695; Willhite et al *Toxicology and Applied Pharmacology* 1986, 83, 563-575; Howard et al *Toxicology and Applied Pharmacology* 1988, 95, 122-138).

There exists therefore a need to improve upon the prior art in order to enhance the clinical profile of such therapeutics. Such improvements may be carried out by introducing specially designed functional groups at specific positions on the molecular backbone of the modulator. The novel compounds of this invention address this issue and display enhanced in vitro profiles when compared to compounds of the prior art.

SUMMARY OF THE INVENTION

This invention provides novel therapeutic agents for the treatment of cancer, metabolic diseases and skin disorders in mammalian subjects. These novel agents bear specially designed functional groups at specific positions on the molecular backbone of the modulator. Such modifications provide additional interactions between the compounds of this invention and certain amino acid residues in the binding pocket of the Retinoid Nuclear receptors. Certain compounds of this invention may also be non-teratogenic retinoid analogs. Such compounds would provide a major public health advantage for mammalian subjects suffering from cancer, metabolic diseases and skin disorders.

As a result, the compounds of this invention show enhanced in vitro and in vivo profiles.

The invention also provides novel compounds that interact with one or more cellular receptors and are useful in the modulation of gene expression.

Furthermore, the invention also provides novel compounds that are useful in controlling cell cycle, and cell differentiation processes regulated by certain hormones, such as for example the thyroid hormone and the like, and/or certain vitamins, such as for example vitamin D and the like, and/or certain retinoids, such as for example 9-cis-retinoic acid and the like.

Furthermore, the invention also provides novel compounds that are useful in inducing apoptosis in mammalian cells.

Furthermore, the invention also provides novel compounds that are useful in treating skin disorders in mammalian subjects.

Furthermore, the invention also provides novel chemical compositions and discloses synthetic methodologies to prepare the same.

In one aspect, the invention relates to novel compounds having the structural formula 1:

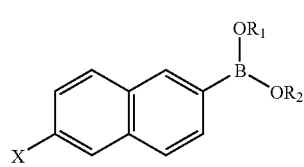

Formula 1 wherein, $R_1$ and $R_2$ are selected from the group consisting of Hydrogen, alkyl, aryl and heteroaryl; $R_1$ and $R_2$ may be linked together to form a substituted or unsubstituted 5- or 6-membered cycloalkyl or cycloalkenyl ring, where said substituents are described as herein, X is selected from a group consisting of the structural formula 2, and structural formula 3:

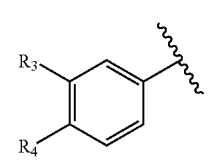

Formula 2

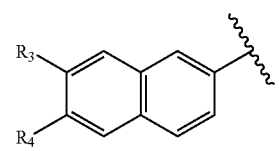

Formula 3 wherein, $R_3$ is selected from a group consisting of Hydrogen, alkyl, adamantyl, alkyloxy, alkylthio, halogen, aryl, aryloxy, arylthio, and heteroaryl;

$R_4$ is selected from a group consisting of Hydrogen, hydroxy, alkyl, alkyloxy, alkylthio, aryl, aryloxy, arylthio and heteroaryl; or $R_3$ and $R_4$ may be linked together to form a substituted or unsubstituted 5- or 6-membered cycloalkyl or cycloalkenyl ring, where said substituents are selected from a group consisting of —OH, =O, halogen, and alkyl, and where one of the Carbon atoms on said 5- or 6-membered cycloalkyl or cycloalkenyl ring may be optionally replaced by W where W is selected from a group consisting of O, S, N, NH, alkylamino, and arylamino;

and pharmaceutically acceptable salts, solvates, and prodrugs thereof.

The non-limiting examples shown in schemes 1-2, illustrate some methods that can be used for carrying out the preparative process of the invention. In schemes 1 and 2, PG represents a hydroxyl protecting group as defined herein, and $R_6$ is selected from a group consisting of alkyl, and aryl.

Scheme 1

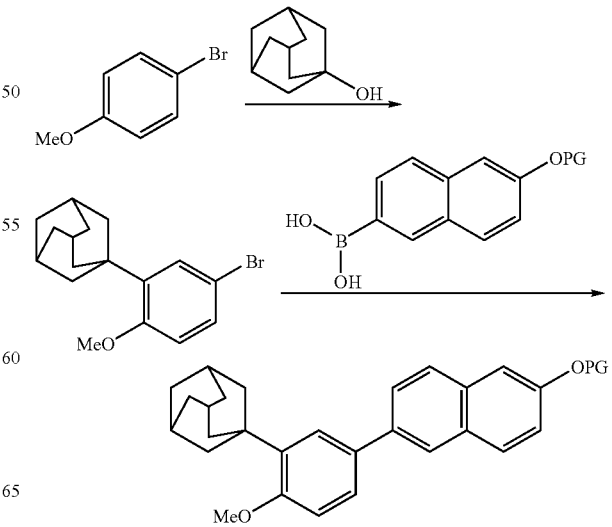

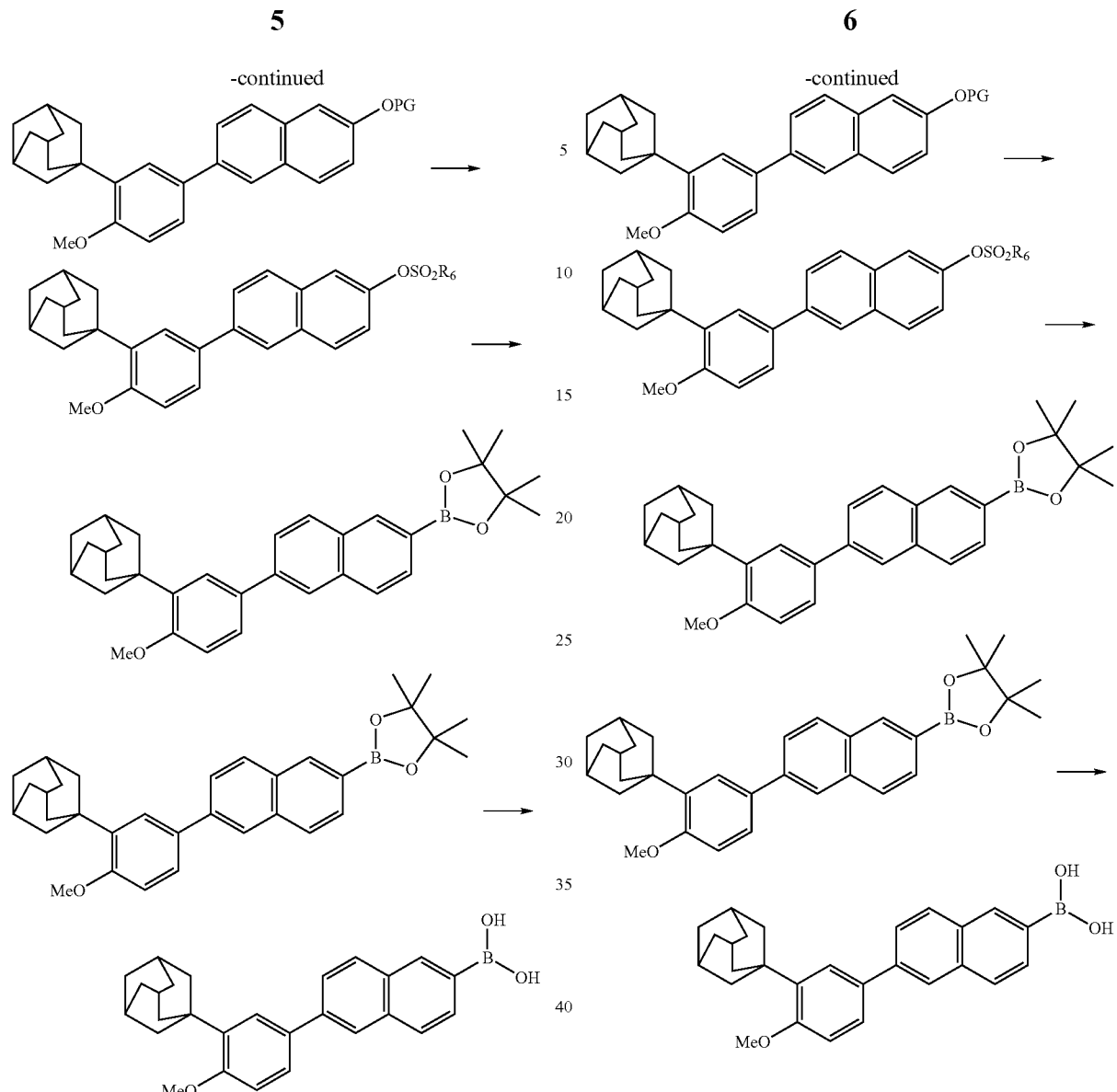

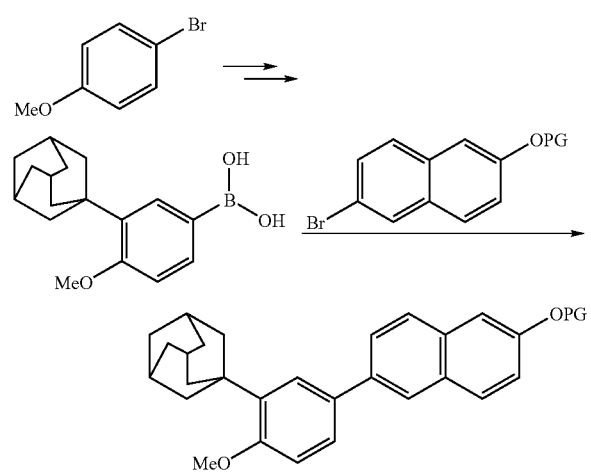

In another aspect, the invention relates to pharmaceutical compositions containing the novel compounds of the invention and to methods of using these compounds for modulating and controlling cell cycle, cell differentiation and apoptosis processes regulated by certain hormones, such as for example the thyroid hormone and the like, and/or certain vitamins, such as for example vitamin D and the like, and/or certain retinoids, such as for example 9-cis-retinoic acid and the like.

In another aspect, the invention relates to pharmaceutical compositions containing the novel compounds of the invention and to methods of using these compounds for modulating and controlling cell cycle, cell differentiation and apoptotic processes regulated by certain genes, such as for example the Fibroblast Growth Fact Binding Protein mRNA, and the like, and/or certain Signal Transducers and Activators of Transcription, such as for example STAT3, and the like, and/or certain proteins, such as for example Cyclin Dependent Kinase (CDK), Transforming Growth Factor alpha (TGF-α), and the like, and/or certain receptors, such as for example Transforming Growth Factor Receptor (TGFR), Endothelial Growth Factor Receptor (EGFR), Retinoid X Receptor (RXR) and the like.

In another aspect, the invention relates to pharmaceutical compositions containing the novel compounds of the invention and to methods of using these compounds to modulate selective gene expression by one or more cellular receptors.

In another aspect, the invention relates to pharmaceutical compositions containing the novel compounds of the invention and to methods of treating diseases and/or conditions using the same. Examples of such disorders include proliferative disorders, differentiation disorders, cancer, mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia, diabetes, inflammatory diseases, cardiovascular diseases, plasma HDL levels, apolipoprotein A1 metabolism, hyperlipidemia, lipid metabolism, lipid homeostasis, hyperlipidemia, skin-related processes, acne, psoriasis, aging, wrinkling, autoimmune diseases, fatty acid metabolism, malignant cell development, premalignant lesions, programmed cell death, endocrinological processes, AP-1 metabolism, hyperglycemia, bone calcification, thyroid conditions and the like.

In yet another aspect, the invention relates to pharmaceutical compositions containing the novel compounds of the invention in combination with other therapeutic agents and to methods of treating diseases and/or conditions using the same. Example of diseases and/or conditions include cancer, mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia and the like. Examples of other therapeutic agents include Busulfan, Carboplatin, Cisplatin, Cyclophosphamide, Cytosine arabinoside, Etoposide, 5-Fluorouracil, Melphalan, Methotrexate, Mitoxantrone, Taxol, Irinotican, Gemzar, Irinotican, Gemzar, Interferon, Fareston, Arzoxifene, Evista, Tamoxifen, and the like.

The invention further provides pharmaceutical compositions containing one or more of the novel compounds as well as pharmaceutically acceptable pro-drugs and salts of such compounds.

Additional features of the invention are set forth in part in the detailed description which follows.

DETAILED DESCRIPTION OF THE INVENTION

In one embodiment of the invention, there are provided compounds having the structural formula 1:

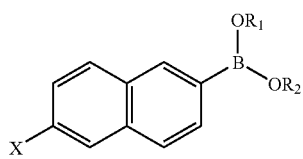

Formula 1 wherein, $R_1$ and $R_2$ are selected from the group consisting of Hydrogen, alkyl, aryl and heteroaryl; $R_1$ and $R_2$ may be linked together to form a substituted or unsubstituted 5- or 6-membered cycloalkyl or cycloalkenyl ring, where said substituents are described as herein, and X is selected from a group consisting of the structural formula 2, and structural formula 3:

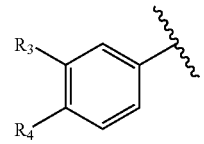

Formula 2

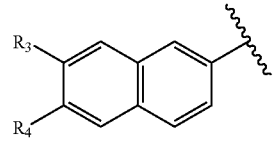

Formula 3 wherein, $R_3$ is selected from a group consisting of Hydrogen, alkyl, adamantyl, alkyloxy, alkylthio, halogen, aryl, aryloxy, arylthio, and heteroaryl;

$R_4$ is selected from a group consisting of Hydrogen, hydroxy, alkyl, alkyloxy, alkylthio, aryl, aryloxy, arylthio and heteroaryl; or $R_3$ and $R_4$ may be linked together to form a substituted or unsubstituted 5- or 6-membered cycloalkyl or cycloalkenyl ring, where said substituents are selected from a group consisting of —OH, =O, halogen, and alkyl, and where one of the Carbon atoms on said 5- or 6-membered cycloalkyl or cycloalkenyl ring may be optionally replaced by W where W is selected from a group consisting of O, S, N, NH, alkylamino, and arylamino;

and pharmaceutically acceptable salts, solvates, and pro-drugs thereof.

In certain embodiments of the invention, $R_1$ is Hydrogen. In other embodiments of the invention, $R_2$ is Hydrogen. In yet other embodiments of the invention, $R_1$ and $R_2$ are both Hydrogens. In certain embodiments of the invention, $R_1$ is alkyl. In other embodiments of the invention, $R_2$ is alkyl. In still other embodiments of the invention, $R_1$ and $R_2$ are linked together to form a substituted or unsubstituted 5- or 6-membered cycloalkyl. In yet other embodiments of the invention, $R_1$ and $R_2$ are linked together to form

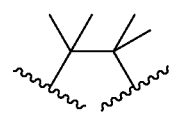

In some embodiments of the invention, $R_3$ is allyl. In certain embodiments of the invention, $R_4$ is adamantyl. In other embodiments of the invention, $R_3$ is tert-butyl. In still other embodiments of the invention, $R_3$ is methyl. In yet other embodiments of the invention, $R_3$ is isopropyl. In certain embodiments of the invention, $R_3$ is cyclohexyl. In other embodiments of the invention, $R_3$ is 1-methylcyclohexyl.

In some embodiments of the invention, $R_4$ is alkyloxy. In certain embodiments of the invention, $R_4$ is methoxy.

In some embodiments of the invention, $R_4$ is alkylthio. In certain embodiments of the invention, $R_4$ is adamantylthio.

In some embodiments of the invention, $R_4$ is substituted alkyl. In certain embodiments of the invention, $R_4$ is —CH$_2$OH. In other embodiments of the invention, $R_4$ is —CH$_2$CH$_2$CH$_2$OH. In still other embodiments of the invention, $R_4$ is —CH(OH)CH$_2$OH. In yet other embodiments of the invention, $R_4$ is —CH$_2$CH(OH)CH$_2$OH.

In certain embodiments of the invention, $R_3$ is alkyl. In other embodiments of the invention, $R_4$ is alkyl. In still other embodiments of the invention, $R_3$ and $R_4$ are linked together to form a substituted or unsubstituted 5- or 6-membered cycloalkyl. In yet other embodiments of the invention, $R_3$ and $R_4$ are linked together to form

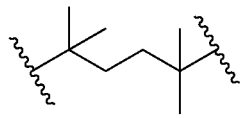

In certain embodiments of the invention, $R_1$ is not Hydrogen. In other embodiments of the invention, $R_2$ is not Hydrogen. In yet other embodiments of the invention, $R_1$ and $R_2$ are both Hydrogens. In certain embodiments of the invention, $R_1$ is not alkyl. In other embodiments of the invention, $R_2$ is not alkyl. In still other embodiments of the invention, $R_1$ and $R_2$ are not linked together to form a substituted or unsubstituted 5- or 6-membered cycloalkyl. In yet other embodiments of the invention, $R_1$ and $R_2$ are not linked together to form

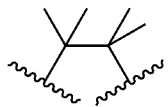

In some embodiments of the invention, $R_3$ is not alkyl. In certain embodiments of the invention, $R_4$ is not adamantyl. In other embodiments of the invention, $R_3$ is not tert-butyl. In still other embodiments of the invention, $R_3$ is not methyl. In yet other embodiments of the invention, $R_3$ is not isopropyl. In certain embodiments of the invention, $R_3$ is not cyclohexyl. In other embodiments of the invention, $R_3$ is not 1-methylcyclohexyl.

In some embodiments of the invention, $R_4$ is not alkyloxy. In certain embodiments of the invention, $R_4$ is not methoxy.

In some embodiments of the invention, $R_4$ is not alkylthio. In certain embodiments of the invention, $R_4$ is not adamantylthio.

In some embodiments of the invention, $R_4$ is not substituted alkyl. In certain embodiments of the invention, $R_4$ is not —$CH_2OH$. In other embodiments of the invention, $R_4$ is not —$CH_2CH_2CH_2OH$. In still other embodiments of the invention, $R_4$ is not —$CH(OH)CH_2OH$. In yet other embodiments of the invention, $R_4$ is not —$CH_2CH(OH)CH_2OH$.

In certain embodiments of the invention, $R_3$ is not alkyl. In other embodiments of the invention, $R_4$ is not alkyl. In still other embodiments of the invention, $R_3$ and $R_4$ are not linked together to form a substituted or unsubstituted 5- or 6-membered cycloalkyl. In yet other embodiments of the invention, $R_3$ and $R_4$ are not linked together to form

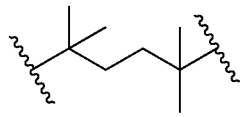

The present invention is intended to include all isotopes of atoms occurring in the present compounds. Isotopes include those atoms having the same atomic number but different mass numbers. By way of general example and without limitation, isotopes of Hydrogen include Deuterium (D) and Tritium (T). Isotopes of Carbon include $^{13}C$ and $^{14}C$. Isotopes of Sulfur include $^{32}S$, $^{33}S$, $^{34}S$, and $^{36}S$. Isotopes of Nitrogen include $^{14}N$ and $^{15}N$. Isotopes of Oxygen include $^{16}O$, $^{17}O$, and $^{18}O$.

Isotopic Hydrogen can be introduced into organic molecules by synthetic techniques and exchange techniques. Synthetic techniques, where Tritium or Deuterium is directly and specifically inserted, may yield high Tritium or Deuterium abundance, but can be limited by the chemistry required. In addition, the molecule being labeled may be changed, depending upon the severity of the synthetic reaction employed. Exchange techniques may yield lower Tritium or Deuterium incorporation, often with the isotope being distributed over many sites on the molecule, but offer the advantage that they do not require separate synthetic steps and are less likely to disrupt the structure of the molecule being labeled.

Unless otherwise indicated, when a substituent is deemed to be "optionally substituted," it is meant that the substituent is a group that may be substituted with one or more group(s) individually and independently selected from the group consisting of Hydrogen, Deuterium, cycloalkyl, aryl, heteroaryl, heterocyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, Protective Groups in Organic Synthesis, $3^{rd}$ Ed., John Wiley & Sons, New York, N.Y., 1999, which is incorporated by reference herein in its entirety.

The compounds according to this invention may contain one or more asymmetric Carbon atoms and can thus occur as racemates and racemic mixtures, single enantiomers, diastereomeric mixtures or individual diastereomers. The term "stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. The compounds described herein may have one or more asymmetrical Carbon atoms and therefore include various stereoisomers. All such isomeric forms of these compounds are expressly included in the present invention.

Each stereogenic Carbon may be of R or S configuration. Although the specific compounds exemplified in this application may be depicted in a particular configuration, compounds having either the opposite stereochemistry at any given chiral center or mixtures thereof are also envisioned. When chiral centers are found in the derivatives of this invention, it is to be understood that this invention encompasses all possible stereoisomers. The terms "optically pure compound" or "optically pure isomer" refers to a single stereoisomer of a chiral compound regardless of the configuration of the said compound.

For purpose of this application, all sugars are referenced using conventional three-letter nomenclature. All sugars are assumed to be in the D-form unless otherwise noted, except for fucose, which is in the L-form. Further, all sugars are in the pyranose form.

The compounds according to this invention may occur as a mixture of tautomers. The term "tautomer" or "tautomerism" refer to one of two or more structural isomers that exist in equilibrium and are readily converted from one isomeric form to another. Examples of include keto-enol tautomers, such as acetone/propen-2-ol and the like, ring-chain tautomers, such as glucose/2,3,4,5,6-pentahydroxy-hexanal and the like. The compounds described herein may have one or more tautomers and therefore include various isomers. All such isomeric forms of these compounds are expressly included in the present invention.

The following example of nomenclature and numbering system is provided for reference.

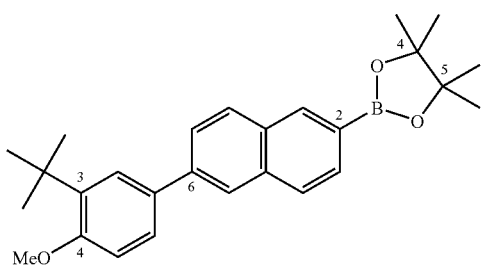

2-[6-(3-tert-Butyl-4-methoxy-phenyl)-naphthalen-2-yl]-
4,4,5,5-tetramethyl-[1,3,2]dioxaborolane The term "substantially homogeneous" refers to collections of molecules wherein at least 80%, preferably at least about 90% and more preferably at least about 95% of the molecules are a single compound or a single stereoisomer thereof.

The term "substantially homogeneous" also refers to collections of molecules wherein at least 80%, preferably at least about 90% and more preferably at least about 95% of the molecules are a single compound or a single stereoisomer thereof, or to collections of molecules wherein at least 80%, preferably at least about 90% and more preferably at least about 95% of the molecules are fully deuterated at the positions stated.

As used herein, the term "attached" signifies a stable covalent bond, certain preferred points of attachment being apparent to those skilled in the art.

The terms "optional" or "optionally" refer to occurrence or non-occurrence of the subsequently described event or circumstance, and that the description includes instances where said event or circumstance occurs and instances where it does not. In such context, the sentence "optionally substituted alkyl group" means that the alkyl group may or may not be substituted and the description includes both a substituted and an unsubstituted alkyl group.

The term "effective amount" of a compound refers a non-toxic but sufficient amount of the compound that provides a desired effect. This amount may vary from subject to subject, depending on the species, age, and physical condition of the subject, the severity of the disease that is being treated, the particular compound used, its mode of administration, and the like. Therefore, it is difficult to generalize an exact "effective amount", yet, a suitable effective amount may be determined by one of ordinary skill in the art.

The term "pharmaceutically acceptable" refers to a compound, additive or composition that is not biologically or otherwise undesirable. For example, the additive or composition may be administered to a subject along with a compound of the invention without causing any undesirable biological effects or interacting in an undesirable manner with any of the other components of the pharmaceutical composition in which it is contained.

The term "pharmaceutically acceptable salts" includes hydrochloric salt, hydrobromic salt, hydroiodic salt, hydrofluoric salt, sulfuric salt, citric salt, maleic salt, acetic salt, lactic salt, nicotinic salt, succinic salt, oxalic salt, phosphoric salt, malonic salt, salicylic salt, phenylacetic salt, stearic salt, pyridine salt, ammonium salt, piperazine salt, diethylamine salt, nicotinamide salt, formic salt, urea salt, sodium salt, potassium salt, calcium salt, magnesium salt, zinc salt, lithium salt, cinnamic salt, methylamino salt, methanesulfonic salt, picric salt, tartaric salt, triethylamino salt, dimethylamino salt, tris(hydroxymethyl)aminomethane salt and the like. Additional pharmaceutically acceptable salts are known to those of skill in the art.

When used in conjunction with a compound of this invention, the terms "elicite," "eliciting," "modulator," "modulate," "modulating," "regulator," "regulate" or "regulating" selective gene expression refer to a compound that can act as an activator, an agonist, a pan-agonist or an antagonist of gene expression by a particular receptor, such as for example a Retinoid X Receptor and the like.

The terms "drug", "therapeutic agent" and "chemotherapeutic agent", refer to a compound or compounds and pharmaceutically acceptable compositions thereof that are administered to mammalian subjects as prophylactic or remedy in the treatment of a disease or medical condition. Such compounds may be administered to the subject via oral formulation, transdermal formulation or by injection.

The term "subject" refers to an animal, preferably a mammal, and most preferably a human, who is the object of treatment, observation or experiment. The mammal may be selected from the group consisting of mice, rats, rabbits, guinea pigs, dogs, cats, sheep, goats, cows, primates, such as monkeys, chimpanzees, and apes, and humans.

The term "therapeutically effective amount" is used to indicate an amount of an active compound, or pharmaceutical agent, that elicits the biological or medicinal response indicated. This response may occur in a tissue, system, animal or human that is being sought by a researcher, veterinarian, medical doctor or other clinician.

The terms "treating," "treatment," "therapeutic," or "therapy" do not necessarily mean total loss of symptoms or nociception. Any alleviation of any undesired signs or symptoms of a disease, such as cancer, acne, psoriasis, or a subset of these conditions, to any extent can be considered treatment or therapy. Furthermore, treatment may include acts that may worsen the patient's overall feeling of well being or appearance.

The term "Lewis acid" refers to a molecule that can accept an unshared pair of electrons and as such would be obvious to one of ordinary skill and knowledge in the art. The definition of "Lewis acid" includes but is not limited to: boron trifluoride, boron trifluoride etherate, boron trifluoride tetrahydrofuran complex, boron trifluoride tert-butyl-methyl ether complex, boron trifluoride dibutyl ether complex, boron trifluoride dihydrate, boron trifluoride di-acetic acid complex, boron trifluoride dimethyl sulfide complex, boron trichloride, boron trichloride dimethyl sulfide complex, boron tribromide, boron tribromide dimethyl sulfide complex, boron triiodide, triimethoxyborane, triethoxyborane, trimethylaluminum, triethylaluminum, aluminum trichloride, aluminum trichloride tetrahydrofuran complex, aluminum tribromide, titanium tetrachloride, titanium tetrabromide, titanium iodide, titanium tetraethoxide, titanium tetraisopropoxide, scandium (III) trifluoromethanesulfonate, yttrium (III) trifluoromethanesulfonate, ytterbium (III) trifluoromethanesulfonate, lanthanum (III) trifluoromethanesulfonate, zinc (II) chloride, zinc (II) bromide, zinc (II) iodide, zinc (II) trifluoromethanesulfonate, zinc (II) sulfate, magnesium sulfate, lithium perchlorate, copper (II) trifluoromethanesulfonate, copper (II) arylcarbonyl hydrazine, hydrazine anion, alkyl hydrazine anion, arylhydrazine anion, alkylcarbonyl hydrazine anion, arylcarbonyl hydrazine anion, cyanide, azide, hydride, alkyl anion, aryl anion and the like.

The term "electrophile" or "electrophilic reagent" refers to a positively charged or neutral molecule that has an open valence shell and as such would be obvious to one of ordinary skill and knowledge in the art. The definition of "electrophile" includes but is not limited to: hydronium, acylium, lewis acids, such as for example, boron trifluoride and the like, halogens, such as for example $Br_2$ and the like, carbocations, such as for example tert-butyl cation and the like, diazomethane, trimethylsilyldiazomethane, alkyl halides, such as for example methyl iodide, benzyl bromide and the like, alkyl triflates, such as for example methyl triflate and the like, alkyl sulfonates, such as for example ethyl toluenesulfonate, butyl methanesulfonate and the like, acyl halides, such as for example acetyl chloride, benzoyl bromide and the like, acid anhydrides, such as for example acetic anhydride, succinic anhydride, maleic anhydride and the like, isocyanates, such as for example methyl isocyanate, phenylisocyanate and the like, chloroformates, such as for example methyl chloroformate, ethyl chloroformate, benzyl chloroformate and the like, sulfonyl halides, such as for example methanesulfonyl chloride, p-toluenesulfonyl chloride and the like, silyl halides, such as for example trimethylsilyl chloride, tertbutyldimethyl silyl chloride and the like, phosphoryl halide such as for example dimethyl chlorophosphate and the like, alpha-beta-unsaturated carbonyl compounds such as for example acrolein, methyl vinyl ketone, cinnamaldehyde and the like.

The term "leaving group" refers to any atom (or group of atoms) that is stable in its anion or neutral form after it has been displaced by a nucleophile and as such would be obvious to one of ordinary skill and knowledge in the art. The definition of "leaving group" includes but is not limited to: water, methanol, ethanol, chloride, bromide, iodide, methanesulfonate, tolylsulfonate, trifluoromethanesulfonate, acetate, trichloroacetate, benzoate and the like.

The term "oxidant" refers to any reagent that will increase the oxidation state of a Carbon atom in the starting material by either adding an oxygen atom to this Carbon or removing an electron from this Carbon and as such would be obvious to one of ordinary skill and knowledge in the art. The definition of "oxidant" includes but is not limited to: osmium tetroxide, ruthenium tetroxide, ruthenium trichloride, potassium permanganate, meta-chloroperbenzoic acid, Hydrogen peroxide, dimethyl dioxirane and the like.

The term "metal ligand" refers to a molecule that has an unshared pair of electrons and can coordinate to a metal atom and as such would be obvious to one of ordinary skill and knowledge in the art. The definition of "metal ligand" includes but is not limited to: water, alkoxy anion, alkylthio anion, ammonia, trialkylamine, triarylamine, trialkylphosphine, triarylphosphine, cyanide, azide and the like.

The term "reducing reagent" refers to any reagent that will decrease the oxidation state of a Carbon atom in the starting material by either adding a Hydrogen atom to this Carbon or adding an electron to this Carbon and as such would be obvious to one of ordinary skill and knowledge in the art. The definition of "reducing reagent" includes but is not limited to: borane-dimethyl sulfide complex, 9-borabicyclo[3.3.1.] nonane (9-BBN), catechol borane, lithium borohydride, sodium borohydride, sodium borohydride-methanol complex, potassium borohydride, sodium hydroxyborohydride, lithium triethylborohydride, lithium n-butylborohydride, sodium cyanoborohydride, calcium (II) borohydride, lithium aluminum hydride, diisobutylaluminum hydride, n-butyl-diisobutylaluminum hydride, sodium bis-methoxyethoxyaluminum hydride, triethoxysilane, diethoxymethylsilane, lithium hydride, lithium, sodium, Hydrogen Ni/B, and the like. Certain acidic and Lewis acidic reagents enhance the activity of reducing reagents. Examples of such acidic reagents include: acetic acid, methanesulfonic acid, hydrochloric acid, and the like. Examples of such Lewis acidic reagents include: trimethoxyborane, triethoxyborane, aluminum trichloride, lithium chloride, vanadium trichloride, dicyclopentadienyl titanium dichloride, cesium fluoride, potassium fluoride, zinc (II) chloride, zinc (II) bromide, zinc (II) iodide, and the like.

The term "coupling reagent" refers to any reagent that will activate the carbonyl of a carboxylic acid and facilitate the formation of an ester or amide bond. The definition of "coupling reagent" includes but is not limited to: acetyl chloride, ethyl chloroformate, dicyclohexylcarbodiimide (DCC), diisopropyl carbodiimide (DIC), 1-ethyl-3-(3-dimethylaminopropyl)carbodiimide (EDCI), N-hydroxybenzotriazole (HOBT), N-hydroxysuccinimide (HOSu), 4-nitrophenol, pentafluorophenol, 2-(1H-benzotriazole-1-yl)-1,1,3,3-tetramethyluronium tetrafluoroborate (TBTU), O-benzotriazole-N,N,N'N'-tetramethyluronium hexafluorophosphate (HBTU), benzotriazole-1-yl-oxy-tris-(dimethylamino)-phosphonium hexafluorophosphate (BOP), benzotriazole-1-yl-oxy-tris-pyrrolidinophosphonium hexafluorophosphate, bromo-trispyrrolidino-phosphonium hexafluorophosphate, 2-(5-norbornene-2,3-dicarboximido)-1,1,3,3-tetramethyluronium tetrafluoroborate (TNTU), O—(N-succinimidyl)-1,1,3,3-tetramethyluronium tetrafluoroborate (TSTU), tetramethylfluoroformamidinium hexafluorophosphate and the like.

The term "removable protecting group" or "protecting group" refers to any group which when bound to a functionality, such as the oxygen atom of a hydroxyl or carboxyl group or the nitrogen atom of an amino group, prevents reactions from occurring at these functional groups and which protecting group can be removed by conventional chemical or enzymatic steps to reestablish the functional group. The particular removable protecting group employed is not critical.

The definition of "hydroxyl protecting group" includes but is not limited to:

a) Methyl, tert-butyl, allyl, propargyl, p-chlorophenyl, p-methoxyphenyl, p-nitrophenyl, 2,4-dinitrophenyl, 2,3,5,6-tetrafluoro-4-(trifluoromethyl)phenyl, methoxymethyl, methylthiomethyl, (phenyldimethylsilyl)methoxymethyl, benzyloxymethyl, p-methoxy-benzyloxymethyl, p-nitrobenzyloxymethyl, o-nitrobenzyloxymethyl, (4-methoxyphenoxy)methyl, guaiacolmethyl, tert-butoxymethyl, 4-pentenyloxymethyl, tert-butyldimethylsiloxymethyl, thexyldimethiylsiloxymethyl, tert-butyldiphenylsiloxymethyl, 2-methoxyethoxymethyl, 2,2,2-trichloroethoxymethyl, bis(2-chloroethoxy)methyl, 2-(trimethylsilyl) ethoxymethyl, menthoxymethyl, 1-ethoxyethyl, 1-(2-chloroethoxy)ethyl, 1-[2-(trimethylsilyl)ethoxy]ethyl, 1-methyl-1-ethoxyethyl, 1-methyl-1-benzyloxyethyl, 1-methyl-1-benzyloxy-2-fluoroethyl, 1-methyl-1-phenoxyethyl, 2,2,2-trichloroethyl, 1-dianisyl-2,2,2-trichloroethyl, 1,1,1,3,3,3-hexafluoro-2-phenylisopropyl, 2-trimethylsilylethyl, 2-(benzylthio)ethyl, 2-(phenylselenyl)ethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetralydropyranyl S,S-dioxide, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothiofuranyl and the like;

b) Benzyl, 2-nitrobenzyl, 2-trifluoromethylbenzyl, 4-methoxybenzyl, 4-nitrobenzyl, 4-chlorobenzyl, 4-bromobenzyl, 4-cyanobenzyl, 4-phenylbenzyl, 4-acylaminobenzyl, 4-azidobenzyl, 4-(methylsulfinyl)benzyl, 2,4-dimethoxybenzyl, 4-azido-3-chlorobenzyl, 3,4-dimethoxybenzyl, 2,6-dichlorobenzyl, 2,6-difluorobenzyl, 1-pyrenylmethyl, diphenylmethyl, 4,4'-dinitrobenzhydryl, 5-benzosuberyl, triphenylmethyl(Trityl), □-naphthyldiphenylmethyl, (4-Methoxyphenyl)-diphenyl-methyl, di-(p-methoxyphenyl)-phenylmethyl, tri-(p-methoxyphenyl)methyl, 4-(4'-bromophenacyloxy)-phenyldiphenylmethyl, 4,4',4"-tris(4,5-dichlorophthalimidophenyl)methyl, 4,4',4"-tris(levulinoyloxyphenyl)methyl, 4,4'-dimethoxy-3"-[N-(imidazolylmethyl)]trityl, 4,4'-dimethoxy-3"-[N-(imidazolylethyl)carbamoyl]trityl, 1,1-bis(4-methoxyphenyl)-1'-pyrenylmethyl, 4-(17-tetrabenzo[a,c,g,I]fluorenylmethyl)-4,4'-dimethoxytrityl, 9-anthryl, 9-(9-phenyl)xanthenyl, 9-(9-phenyl-10-oxo)anthryl and the like;

c) Trimethylsilyl, triethylsilyl, triisopropylsilyl, dimethylisopropylsilyl, diethylisopropylsilyl, dimethylhexylsilyl, tert-butyldimethylsilyl, tert-butyldiphenylsilyl, tribenzylsilyl, tri-p-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenylsilyl, tert-butoxydiphenylsilyl and the like;

d) —C(O)$R_{20}$, where $R_{20}$ is selected from alkyl, substituted alkyl, aryl and more specifically $R_{20}$=Hydrogen, methyl, ethyl, tert-butyl, adamantyl, crotyl, chloromethyl, dichloromethyl, trichloromethyl, trifluoromethyl, methoxymethyl, triphenylmethoxymethyl, phenoxymethyl, 4-chlorophenoxymethyl, phenylmethyl, diphenylmethyl, 4-methoxycrotyl, 3-phenylpropyl, 4-pentenyl, 4-oxopentyl, 4,4-(ethylenedithio)pentyl, 5-[3-bis(4-methoxyphenyl)hydroxymethylphenoxy]-4-oxopentyl, phenyl, 4-methylphenyl, 4-nitrophenyl, 4-fluorophenyl, 4-chlorophenyl, 4-methoxyphenyl, 4-phenylphenyl, 2,4,6-trimethylphenyl, α-naphthyl, benzoyl and the like;

e) —C(O)O$R_{20}$, where $R_{20}$ is selected from alkyl, substituted alkyl, aryl and more specifically $R_{20}$=methyl, methoxymethyl, 9-fluorenylmethyl, ethyl, 2,2,2-trichloroethyl, 1,1-dimethyl-2,2,2-trichloroethyl, 2-(trimethylsilyl)ethyl, 2-(phenylsulfonyl)ethyl, isobutyl, tert-Butyl, vinyl, allyl, 4-nitrophenyl, benzyl, 2-nitrobenzyl, 4-nitrobenzyl, 4-methoxybenzyl, 2,4-dimethoxybenzyl, 3,4-dimethoxybenzyl, 2-(methylthiomethoxy)ethyl, 2-dansenylethyl, 2-(4-nitrophenyl)ethyl, 2-(2,4-dinitrophenyl)ethyl, 2-cyano-1-phenylethyl, thiobenzyl, 4-ethoxy-1-naphthyl and the like.

The definition of "amino protecting group" includes but is not limited to:

a) 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 1-methyl-1-(triphenylphosphonio)ethyl, 1,1-dimethyl-2-cyanoethyl, 2-dansylethyl, 2-(4-nitrophenyl)ethyl, 4-phenylacetoxybenzyl, 4-azidobenzyl, 4-azidomethoxybenzyl, m-chloro-p-acyloxybenzyl, p-(dihydroxyboryl)benzyl, 5-benzisoxazolylmethyl, 2-(trifluoromethyl)-6-chromonylmethyl, m-nitrophenyl, 3,5-dimethoxybenzyl, 1-methyl-1-(3,5-dimethoxyphenyl)ethyl, o-nitrobenzyl, α-methylnitropiperonyl, 3,4-dimethoxy-6-nitrobenzyl, N-benzenesulfenyl, N-o-nitrobenzenesulfenyl, N-2,4-dinitrobenzenesulfenyl, N-pentachlorobenzenesulfenyl. N-2-nitro-4-methoxybenzenesulfenyl, N-triphenylmethylsulfenyl, N-1-(2,2,2-trifluoro-1,1-diphenyl)ethylsulfenyl, N-3-nitro-2-pyridinesulfenyl, N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6-tetramethyl-4-methoxybenzenesulfonyl and the like;

b) —C(O)O$R_{20}$, where $R_{20}$ is selected from alkyl, substituted alkyl, aryl and more specifically $R_{20}$=methyl, ethyl, 9-fluorenylmethyl, 9-(2-sulfo)fluorenylmethyl. 9-(2,7-dibromo)fluorenylmethyl, 17-tetrabenzo[a,c,g,i]fluorenylmethyl. 2-chloro-3-indenylmethyl, benz[f]linden-3-ylmethyl, 2,7-di-t-butyl-[9-(10,10-dioxo-10,10,10,10-tetrahydrothloxanthyl)]methyl, 1,1-dioxobenzo[b]thiophene-2-ylmethyl, 2,2,2-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-tert-butylphenyl)-1-methylethyl, 2-(2'-pyridyl)ethyl, 2-(4'-pyridyl)ethyl, 2,2-bis(4'-nitrophenyl)ethyl, N-(2-pivaloylamino)-1,1-dimethylethyl, 2-[(2-nitrophenyl)dithio]-1-phenylethyl, tert-butyl, 1-adamantyl, 2-adamantyl, Vinyl, allyl, 1-Isopropylallyl, cinnamyl. 4-nitrocinnamyl, 3-(3'-pyridyl)prop-2-enyl, 8-quinolyl, N-Hydroxypiperidinyl, alkyldithio, benzyl, p-methoxybenzyl, p-nitrobenzyl, p-bromobenzyl. p-chlorobenzyl, 2,4-dichlorobenzyl, 4-methylsulfinylbenzyl, 9-anthrylmethyl, diphenylmethyl, tert-amyl, S-benzyl thiocarbamate, butynyl, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N'-dimethylcarboxamido)benzyl, 1,1-dimethyl-3-(N,N'-dimethylcarboxamido)propyl, 1,1-dimethylpropynyl, di(2-pyridyl)methyl, 2-furanylmethyl, 2-lodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(p-phenylazophenyl)ethyl, 1-methyl-1-phenylethyl, 1-methyl-1-4'-pyridylethyl, phenyl, p-(phenylazo)benzyl, 2,4,6-trimethylphenyl, 4-(trimethylammonium)benzyl, 2,4,6-trimethylbenzyl and the like.

The definition of "carboxyl protecting group" includes but is not limited to:

2-N-(morpholino)ethyl, choline, methyl, methoxyethyl, 9-Fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, pivaloyloxymethyl, phenylacetoxymethyl, triisopropylsilylmethyl, cyanomethyl, acetol, p-bromophenacyl. α-methylphenacyl, p-methoxyphenacyl, desyl, carboxamidomethyl, p-azobenzenecarboxamido-methyl, N-phthalimidomethyl, (methoxyethoxy)ethyl, 2,2,2-trichloroethyl, 2-fluoroethyl, 2-chloroethyl, 2-bromoethyl, 2-iodoethyl, 4-chlorobutyl, 5-chloropentyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl, 2-cyanoethyl, heptyl, tert-butyl, 3-methyl-3-pentyl, dicyclopropylmethyl, 2,4-dimethyl-3-pentyl, cyclopentyl, cyclohexyl, allyl, methallyl, 2-methylbut-3-en-2-yl, 3-methylbut-2-(prenyl), 3-buten-1-yl, 4-(trimethylsilyl)-2-buten-1-yl, cinnamyl, α-methylcinnamyl, propargyl, phenyl, 2,6-dimethylphenyl, 2,6-diisopropylphenyl, 2,6-di-tert-butyl-4-methylphenyl, 2,6-di-tert-butyl-4-methoxyphenyl, p-(methylthio)phenyl, pentafluorophenyl, benzyl, triphenylmethyl, diphenylmethyl, bis(o-nitrophenyl)methyl, 9-anthrylmethyl, 2-(9,10-dioxo)anthrylmethyl. 5-dibenzosuberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-Sulfobenzyl, 4-azidomethoxybenzyl, 4-{a/-[1-(4,4-dimethyl-2,6-dioxocyclohexylidene)-3-methylbutyl]
amino}benzyl, piperonyl, 4-picolyl, trimethylsilyl, triethylsilyl, tert-butyldimethylsilyl, isopropyldimethylsilyl, phenyldimethylsilyl, di-tert-butylmethylsilyl, triisopropylsilyl and the like.

The term "Amino acid" refers to any of the naturally occurring amino acids, as well as synthetic analogs and derivatives thereof. Alpha-Amino acids comprise a Carbon atom to which is bonded an amino group, a carboxy group, a Hydrogen atom, and a distinctive group referred to as a "side chain". The side chains of naturally occurring amino acids are well known in the art and include, for example, Hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine), substituted arylalkyl (e.g., as in tyrosine), heteroarylalkyl (e.g., as in tryptophan, histidine) and the like. One of skill in the art will appreciate that the term "amino acid" can also include beta-, gamma-, delta-, omega-amino acids, and the like. Unnatural amino acids are also known in the art, as set forth in, Natchus, M. G. Organic Synthesis: Theory and Applications (2001), 5, 89-196; Ager, D. J. Current tetrafluoroborate and the like. Certain Lewis acids may have optically pure ligands attached to the electron acceptor atom, as set forth in Corey, E. J. Angewandte Chemie, International Edition (2002), 41(10), 1650-1667; Aspinall, H. C. Chemical Reviews (Washington, D.C., United States) (2002), 102(6), 1807-1850; Groger, H. Chemistry—A European Journal (2001), 7(24), 5246-5251; Davies, H. M. L. Chemtracts (2001), 14(11), 642-645; Wan, Y. Chemtracts (2001), 14(11), 610-615; Kim, Y. H. Accounts of Chemical Research (2001), 34(12), 955-962; Seebach, D. Angewandte Chemie, International Edition (2001), 40(1), 92-138; Blaser, H. U. Applied Catalysis, A: General (2001), 221(1-2), 119-143; Yet, L. Angewandte Chemie, International Edition (2001), 40(5), 875-877; Jorgensen, K. A. Angewandte Chemie, International Edition (2000), 39(20), 3558-3588; Dias, L. C. Current Organic Chemistry (2000), 4(3), 305-342; Spindler, F. Enantiomer (1999), 4(6), 557-568; Fodor, K. Enantiomer (1999), 4(6), 497-511; Shimizu, K. D.; Comprehensive Asymmetric Catalysis I-III (1999), 3, 1389-1399; Kagan, H. B. Comprehensive Asymmetric Catalysis I-III (1999), 1, 9-30; Mikami, K. Lewis Acid Reagents (1999), 93-136 and all references cited therein. Such Lewis acids maybe used by one of ordinary skill and knowledge in the art to produce optically pure compounds from achiral starting materials.

The term "acylating agent" refers to a molecule that can transfer an alkylcarbonyl, substituted alkylcarbonyl or aryl carbonyl group to another molecule. The definition of "acylating agent" includes but is not limited to ethyl acetate, vinyl acetate, vinyl propionate, vinyl butyrate, isopropenyl acetate, 1-ethoxyvinyl acetate, trichloroethyl butyrate, trifluoroethyl butyrate, trifluoroethyl laureate, S-ethyl thiooctanoate, biacetyl monooxime acetate, acetic anhydride, acetyl chloride, succinic anhydride, diketene, diallyl Carbonate, Carbonic acid but-3-enyl ester cyanomethyl ester, amino acid and the like.

The term "nucleophile" or "nucleophilic reagent" refers to a negatively charged or neutral molecule that has an unshared pair of electrons and as such would be obvious to one of ordinary skill and knowledge in the art. The definition of "nucleophile" includes but is not limited to: water, alkylhydroxy, alkoxy anion, arylhydroxy, aryloxy anion, alkylthiol, alkylthio anion, arylthiol, arylthio anion, ammonia, alkylamine, arylamine, alkylamine anion, arylamine anion, hydrazine, alkyl hydrazine, arylhydrazine, alkylcarbonyl hydrazine, Opinion in Drug Discovery & Development (2001), 4(6), 800; Reginato, G. Recent Research Developments in Organic Chemistry (2000), 4(Pt. 1), 351-359; Dougherty, D. A. Current Opinion in Chemical Biology (2000), 4(6), 645-652; Lesley, S. A. Drugs and the Pharmaceutical Sciences (2000), 101 (Peptide and Protein Drug Analysis), 191-205; Pojitkov, A. E. Journal of Molecular Catalysis B: Enzymatic (2000), 10(1-3), 47-55; Ager, D. J. Specialty Chemicals (1999), 19(1), 10-12, and all references cited therein. Stereoisomers (e.g., D-amino acids) of the twenty conventional amino acids, unnatural amino acids such as alpha, alpha-disubstituted amino acids and other unconventional amino acids may also be suitable components for compounds of the present invention. Examples of unconventional amino acids include: 4-hydroxyproline, 3-methylhistidine, 5-hydroxylysine, and other similar amino acids and imino acids (e.g., 4-hydroxyproline).

The term "N-protected amino acid" refers to any amino acid which has a protecting group bound to the nitrogen of the amino functionality. This protecting group prevents reactions from occurring at the amino functional group and can be removed by conventional chemical or enzymatic steps to reestablish the amino functional group. The particular protecting group employed is not critical.

The term "O-protected amino acid" refers to any amino acid which has a protecting group bound to the oxygen of the carboxyl functionality. This protecting group prevents reactions from occurring at the carboxyl functional group and can be removed by conventional chemical or enzymatic steps to reestablish the carboxyl functional group. The particular protecting group employed is not critical.

The term "Prodrug" refers to an agent that is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A prodrug may be converted into the parent drug by various mechanisms, including enzymatic processes and metabolic hydrolysis. See Harper, "Drug Latentiation" in Jucker, ed. Progress in Drug Research 4:221-294 (1962); Morozowich et al., "Application of Physical Organic Principles to Prodrug Design" in E. B. Roche ed. Design of Biopharmaceutical Properties through Prodrugs and Analogs, APHA Acad. Pharm. Sci. (1977); Bioreversible Carriers in Drug in Drug Design, Theory and Application, E. B. Roche, ed., APHA Acad. Pharm. Sci. (1987); Design of Prodrugs, H. Bundgaard, Elsevier (1985); Wang et al. "Prodrug approaches to the improved delivery of peptide drug" in Curr. Pharm. Design. 5(4):265-287 (1999); Pauletti et al. (1997) Improvement in peptide bioavailability: Peptidomimetics and Prodrug Strategies, Adv. Drug. Delivery Rev. 27:235-256; Mizen et al. (1998) "The Use of Esters as Prodrugs for Oral Delivery of .beta.-Lactam antibiotics," Pharm. Biotech. 11:345-365; Gaignault et al. (1996) "Designing Prodrugs and Bioprecursors I. Carrier Prodrugs," Pract. Med. Chem. 671-696; Asgharnejad, "Improving Oral Drug Transport", in Transport Processes in Pharmaceutical Systems, G. L. Amidon, P. I. Lee and E. M. Topp, Eds., Marcell Dekker, p. 185-218 (2000); Balant et al., "Prodrugs for the improvement of drug absorption via different routes of administration", Eur. J. Drug Metab. Pharmacokinet., 15(2): 143-53 (1990); Balimane and Sinko, "Involvement of multiple transporters in the oral absorption of nucleoside analogues", Adv. Drug Delivery Rev., 39(1-3): 183-209 (1999); Browne, "Fosphenytoin (Cerebyx)", Clin. Neuropharmacol. 20(1): 1-12 (1997); Bundgaard, "Bioreversible derivatization of drugs—principle and applicability to improve the therapeutic effects of drugs", Arch. Pharm. Chemi 86(1): 1-39 (1979); Bundgaard H. "Improved drug delivery by the prodrug approach", Controlled Drug Delivery 17: 179-96 (1987); Bundgaard H. "Prodrugs as a means to improve the delivery of peptide drugs", Adv. Drug Delivery Rev. 8(1): 1-38 (1992); Fleisher et al. "Improved oral drug delivery: solubility limitations overcome by the use of prodrugs", Adv. Drug Delivery Rev. 19(2): 115-130 (1996); Fleisher et al. "Design of prodrugs for improved gastrointestinal absorption by intestinal enzyme targeting", Methods Enzymol. 112 (Drug Enzyme Targeting, Pt. A): 360-81, (1985); Farquhar D, et al., "Biologically Reversible Phosphate-Protective Groups", J. Pharm. Sci., 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," J. Chem. Soc., Chem. Commun., 875-877 (1991); Friis and Bundgaard, "Prodrugs of phosphates and phosphonates: Novel lipophilic alpha-acyloxyalkyl ester derivatives of phosphate- or phosphonate containing drugs masking the negative charges of these groups", Eur. J. Pharm. Sci. 4: 49-59 (1996); Gangwar et al., "Pro-drug, molecular structure and percutaneous delivery", Des. Biopharm. Prop. Prodrugs Analogs, [Symp.] Meeting Date 1976, 409-21. (1977); Nathwani and Wood, "Penicillins: a current review of their clinical pharmacology and therapeutic use", Drugs 45(6): 866-94 (1993); Sinhababu and Thakker, "Prodrugs of anticancer agents", Adv. Drug Delivery Rev. 19(2): 241-273 (1996); Stella et al., "Prodrugs. Do they have advantages in clinical practice?", Drugs 29(5): 455-73 (1985); Tan et al. "Development and optimization of anti-HIV nucleoside analogs and prodrugs: A review of their cellular pharmacology, structure-activity relationships and pharmacokinetics", Adv. Drug Delivery Rev. 39(1-3): 117-151 (1999); Taylor, "Improved passive oral drug delivery via prodrugs", Adv. Drug Delivery Rev., 19(2): 131-148 (1996); Valentino and Borchardt, "Prodrug strategies to enhance the intestinal absorption of peptides", Drug Discovery Today 2(4): 148-155 (1997); Wiebe and Knaus, "Concepts for the design of anti-HIV nucleoside prodrugs for treating cephalic HIV infection", Adv. Drug Delivery Rev.: 39(1-3):63-80 (1999); Waller et al., "Prodrugs", Br. J. Clin. Pharmac. 28: 497-507 (1989).

In light of the purposes described for the present invention, all references to reagents ordinarily containing Hydrogens, hydrides, or protons may include partially or fully deuterated versions (containing Deuterium, deuteride, or deuteronium) as required to effect transformation to the improved drug substances outlined herein.

The terms "halogen", "halide" or "halo" include fluorine, chlorine, bromine, and iodine.

The terms "alkyl" and "substituted alkyl" are interchangeable and include substituted, optionally substituted and unsubstituted $C_1$-$C_{10}$ straight chain saturated aliphatic hydroCarbon groups, substituted, optionally substituted and unsubstituted $C_2$-$C_{10}$ straight chain unsaturated aliphatic hydroCarbon groups, substituted, optionally substituted and unsubstituted $C_4$-$C_{10}$ branched saturated aliphatic hydroCarbon groups, substituted and unsubstituted $C_4$-$C_{10}$ branched unsaturated aliphatic hydroCarbon groups, substituted, optionally substituted and unsubstituted $C_3$-$C_8$ cyclic saturated aliphatic hydroCarbon groups, substituted, optionally substituted and unsubstituted $C_5$-$C_8$ cyclic unsaturated aliphatic hydroCarbon groups having the specified number of Carbon atoms. For example, the definition of "alkyl" shall include but is not limited to: methyl (Me), trideuteromethyl ($-CD_3$), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like. Alkyl substituents are independently selected from the group consisting of Hydrogen, Deuterium, halogen, $-OH$, $-SH$, $-NH_2$, $-CN$, $-NO_2$, $=O$, $=CH_2$, trihalomethyl, carbamoyl, aryl$C_{0-10}$alkyl, heteroaryl$C_{0-10}$alkyl, $C_{1-10}$alkyloxy, aryl$C_{0-10}$alkyloxy, $C_{1-10}$alkylthio, aryl$C_{0-10}$alkylthio, $C_{1-10}$alkylamino, aryl$C_{0-10}$alkylamino, N-aryl-N—$C_{0-10}$alkylamino, $C_{1-10}$alkylcarbonyl, aryl$C_{0-10}$alkylcarbonyl, $C_{1-10}$alkylcarboxy, aryl$C_{0-10}$alkylcarboxy, $C_{1-10}$alkylcarbonylamino, aryl$C_{0-10}$alkylcarbonylamino, tetrahydrofuryl, morpholinyl, piperazinyl, hydroxypyronyl, $-C_{0-10}$alkylCOO$R_{21}$ and $-C_{0-10}$alkylCON$R_{22}R_{23}$ wherein $R_{21}$, $R_{22}$ and $R_{23}$ are independently selected from the group consisting of Hydrogen, Deuterium, alkyl, aryl, or $R_{22}$ and $R_{23}$ are taken together with the Nitrogen to which they are attached forming a saturated cyclic or unsaturated cyclic system containing 3 to 8 Carbon atoms with at least one substituent as defined herein.

In light of the purposes described for the present invention, all references to "alkyl" groups or any groups ordinarily containing C—H bonds may include partially or fully deuterated versions as required to effect the improvements outlined herein.

The term "alkyloxy" (e.g. methoxy, ethoxy, propyloxy, allyloxy, cyclohexyloxy) represents a substituted or unsubstituted alkyl group as defined above having the indicated number of Carbon atoms attached through an oxygen bridge. The term "alkyloxyalkyl" represents an alkyloxy group attached through an alkyl or substituted alkyl group as defined above having the indicated number of Carbon atoms.

The term "alkylthio" (e.g. methylthio, ethylthio, propylthio, cyclohexenylthio and the like) represents a substituted or unsubstituted alkyl group as defined above having the indicated number of Carbon atoms attached through a sulfur bridge. The term "alkylthioalkyl" represents an alkylthio group attached through an allyl or substituted allyl group as defined above having the indicated number of Carbon atoms.

The term "alkylamino" (e.g. methylamino, diethylamino, butylamino, N-propyl-N-hexylamino, (2-cyclopentyl)propylamino, hexenylamino, and the like) represents one or two substituted or unsubstituted alkyl groups as defined above having the indicated number of Carbon atoms attached through an amine bridge. The substituted or unsubstituted alkyl groups maybe taken together with the nitrogen to which they are attached forming a saturated cyclic or unsaturated cyclic system containing 3 to 10 Carbon atoms with at least one substituent as defined above. The term "alkylaminoalkyl" represents an alkylamino group attached through a substituted or unsubstituted alkyl group as defined above having the indicated number of Carbon atoms.

The term "alkylhydrazino" (e.g. methylhydrazino, diethylhydrazino, butylhydrazino, (2-cyclopentyl)propylhydrazino, cyclohexanehydrazino, and the like) represents one or two substituted or unsubstituted alkyl groups as defined above having the indicated number of Carbon atoms attached through a nitrogen atom of a hydrazine bridge. The substituted or unsubstituted alkyl groups may be taken together with the nitrogen to which they are attached forming a saturated cyclic or unsaturated cyclic system containing 3 to 10 Carbon atoms with at least one substituent as defined above. The term "alkylhydrazinoalkyl" represents an alkylhydrazino group attached through a substituted or unsubstituted alkyl group as defined above having the indicated number of Carbon atoms.

The term "alkylcarbonyl" (e.g. cyclooctylcarbonyl, pentylcarbonyl, 3-hexenylcarbonyl and the like) represents a substituted or unsubstituted alkyl group as defined above having the indicated number of Carbon atoms attached through a carbonyl group. The term "alkylcarbonylalkyl" represents an alkylcarbonyl group attached through a substituted or unsubstituted alkyl group as defined above having the indicated number of Carbon atoms.

The term "alkylcarboxy" (e.g. heptylcarboxy, cyclopropylcarboxy, 3-pentenylcarboxy and the like) represents an alkylcarbonyl group as defined above wherein the carbonyl is in turn attached through an oxygen. The term "alkylcarboxyalkyl" represents an alkylcarboxy group attached through an alkyl group as defined above having the indicated number of Carbon atoms.

The term "alkylcarbonylamino" (e.g. hexylcarbonylamino, cyclopentylcarbonyl-aminomethyl, methylcarbonylaminophenyl and the like) represents an alkylcarbonyl group as defined above wherein the carbonyl is in turn attached through the nitrogen atom of an amino group. The nitrogen group may itself be substituted with a substituted or unsubstituted alkyl or aryl group. The term "alkylcarbonylaminoalkyl" represents an alkylcarbonylamino group attached through a substituted or unsubstituted alkyl group as defined above having the indicated number of Carbon atoms.

The term "alkylcarbonylhydrazino" (e.g. ethylcarbonylhydrazino, tert-butylcarbonylhydrazino and the like) represents an alkylcarbonyl group as defined above wherein the carbonyl is in turn attached through the nitrogen atom of a hydrazino group.

The term "aryl" represents an unsubstituted, mono-, di- or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are independently selected from a group consisting of halogen, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N—$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_{21}$, and —CO$_{0-10}$alkylCONR$_{22}$R$_{23}$ wherein R$_{21}$, R$_{22}$ and R$_{23}$ are independently selected from Hydrogen, alkyl, aryl or R$_{22}$ and R$_{23}$ are taken together with the nitrogen to which they are attached forming a saturated cyclic or unsaturated cyclic system containing 3 to 8 Carbon atoms with at least one substituent as defined above.

The definition of "aryl" includes but is not limited to phenyl, biphenyl, naphthyl, dihydronaphthyl, tetrahydronaphthyl, indenyl, indenyl, azulenyl, anthryl, phenanthryl, fluorenyl, pyrenyl and the like.

The term "arylalkyl" (e.g. (4-hydroxyphenyl)ethyl, (2-aminonaphthyl)hexenyl and the like) represents an aryl group as defined above attached through a substituted or unsubstituted alkyl group as defined above having the indicated number of Carbon atoms.

The term "arylcarbonyl" (e.g. 2-thiophenylcarbonyl, 3-methoxyanthrylcarbonyl and the like) represents an aryl group as defined above attached through a carbonyl group.

The term "arylalkylcarbonyl" (e.g. (2,3-dimethoxyphenyl)propylcarbonyl, (2-chloronaphthyl)pentenyl-carbonyl and the like) represents an arylalkyl group as defined above wherein the alkyl group is in turn attached through a carbonyl.

The term "aryloxy" (e.g. phenoxy, naphthoxy, 3-methylphenoxy, and the like) represents an aryl or substituted aryl group as defined above having the indicated number of Carbon atoms attached through an oxygen bridge. The term "aryloxyalkyl" represents an aryloxy group attached through a substituted or unsubstituted alkyl group as defined above having the indicated number of Carbon atoms.

The term "arylthio" (e.g. phenylthio, naphthylthio, 3-bromophenylthio, and the like) represents an aryl or substituted aryl group as defined above having the indicated number of Carbon atoms attached through a sulfur bridge. The term "arylthioalkyl" represents an arylthio group attached through a substituted or unsubstituted alkyl group as defined above having the indicated number of Carbon atoms.

The term "arylamino" (e.g. phenylamino, diphenylamino, naphthylamino, N-phenyl-N-naphthylamino, o-methylphenylamino, p-methoxyphenylamino, and the like) represents one or two aryl groups as defined above having the indicated number of Carbon atoms attached through an amine bridge. The term "arylaminoalkyl" represents an arylamino group attached through a substituted or unsubstituted alkyl group as defined above having the indicated number of Carbon atoms. The term "arylalkylamino" represents an aryl group attached through an alkylamino group as defined above having the indicated number of Carbon atoms. The term "N-aryl-N-alkylamino" (e.g. N-phenyl-N-methylamino, N-naphthyl-N-butylamino, and the like) represents one aryl and one a substituted or unsubstituted alkyl group as defined above having the indicated number of Carbon atoms independently attached through an amine bridge.

The term "arylhydrazino" (e.g. phenylhydrazino, naphthylhydrazino, 4-methoxyphenylhydrazino, and the like) represents one or two aryl groups as defined above having the indicated number of Carbon atoms attached through a hydrazine bridge. The term "arylhydrazinoalkyl" represents an arylhydrazino group attached through a substituted or unsubstituted alkyl group as defined above having the indicated number of Carbon atoms. The term "arylalkylhydrazino" represents an aryl group attached through an alkylhydrazino group as defined above having the indicated number of Carbon atoms. The term "N-aryl-N-alkylhydrazino" (e.g. N-phenyl-N-methylhydrazino, N-naphthyl-N-butylhydrazino, and the like) represents one aryl and one a substituted or unsubstituted alkyl group as defined above having the indicated number of Carbon atoms independently attached through an amine a The term "arylcarboxy" (e.g. phenylcarboxy, naphthylcarboxy, 3-fluorophenylcarboxy and the like) represents an arylcarbonyl group as defined above wherein the carbonyl is in turn attached through an oxygen bridge. The term "arylcarboxyalkyl" represents an arylcarboxy group attached through a substituted or unsubstituted alkyl group as defined above having the indicated number of Carbon atoms.

The term "arylcarbonylamino" (e.g. phenylcarbonylamino, naphthylcarbonylamino, 2-methylphenylcarbonylamino and the like) represents an arylcarbonyl group as defined above wherein the carbonyl is in turn attached through the nitrogen atom of an amino group. The nitrogen group may itself be substituted with an a substituted or unsubstituted alkyl or aryl group. The term "arylcarbonylaminoalkyl" represents an arylcarbonylamino group attached through a substituted or unsubstituted allyl group as defined above having the indicated number of Carbon atoms. The nitrogen group may itself be substituted with a substituted or unsubstituted alkyl or aryl group.

The term "arylcarbonylhydrazino" (e.g. phenylcarbonylhydrazino, naphthylcarbonylhydrazino, and the like) represents an arylcarbonyl group as defined above wherein the carbonyl is in turn attached through the nitrogen atom of a hydrazino group.

The terms "heteroaryl", "heterocycle" or "heterocyclic" refers to a monovalent unsaturated group having a single ring or multiple condensed rings, from 1 to 8 Carbon atoms and from 1 to 4 hetero atoms selected from nitrogen, sulfur or oxygen within the ring. The heteroaryl groups in this invention can be optionally substituted with 1 to 3 substituents selected from a group consisting of: halogen, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N—$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$ alkylcarbonylamino$C_{0-10}$alkyl, —$C_{0-10}$alkyl-COOR$_{21}$, and —$C_{0-10}$alkylCONR$_{22}$R$_{23}$ wherein R$_{21}$, R$_{22}$ and R$_{23}$ are independently selected from Hydrogen, alkyl, aryl, or R$_{22}$ and R$_{23}$ are taken together with the nitrogen to which they are attached forming a saturated cyclic or unsaturated cyclic system containing 3 to 8 Carbon atoms with at least one substituent as defined above.

The definition of "heteroaryl" includes but is not limited to thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl, 2H-imidazolinyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4,5]tetrazinyl-3,6-dione, [1,2,4,5]tetrazinyl-3,6-dione, dihydro-pyrimidinyl-2,4-dione, pyrimidinyl-2,4,6-trione and the like. For the purposes of this application, the terms "heteroaryl", "heterocycle" or "heterocyclic" do not include carbohydrate rings (i.e. mono- or oligosaccharides).

The term "saturated heterocyclic" represents an unsubstituted, mono-, di- or trisubstituted monocyclic, polycyclic saturated heterocyclic group covalently attached at any ring position capable of forming a stable covalent bond, certain preferred points of attachment being apparent to those skilled in the art (e.g., 1-piperidinyl, 4-piperazinyl and the like).

The saturated heterocyclic substituents are independently selected from a group consisting of halo, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N—$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$ alkylcarbonylamino$C_{0-10}$alkyl, —$C_{0-10}$alkyl-COOR$_{21}$, and —$C_{0-10}$alkylCONR$_{22}$R$_{23}$ wherein R$_{21}$, R$_{22}$ and R$_{23}$ are independently selected from Hydrogen, alkyl, aryl, or R$_{22}$ and R$_{23}$ are taken together with the nitrogen to which they are attached forming a saturated cyclic or unsaturated cyclic system containing 3 to 8 Carbon atoms with at least one substituent as defined above.

The definition of saturated heterocyclic includes but is not limited to pyrrolidinyl, pyrazolidinyl, piperidinyl, 1,4-dioxanyl, morpholinyl, 1,4-dithienyl, thiomorpholinyl, piperazinyl, quinuclidinyl, and the like.

The term "alpha-beta-unsaturated carbonyl" refers to a molecule that has a carbonyl group directly attached to a double or triple bonded Carbon and which would be obvious to one of ordinary skill and knowledge in the art. The definition of alpha-beta-unsaturated carbonyl includes but is not limited to acrolein, methyl vinyl ketone, and the like.

The term "acetal" refers to a molecule that contains a Carbon atom $C_1$ that is directly attached to a Hydrogen atom ($H_1$), a substituted Carbon atom ($C_2$) and two Oxygen atoms ($O_1$ and $O_2$). These Oxygen atoms are in turn attached to other substituted Carbon atoms ($C_3$ and $C_4$), which would be obvious to one of ordinary skill and knowledge in the art. The definition of acetal includes but is not limited to 1,1-dimethoxypropane, 1,1-bis-allyloxybutane and the like.

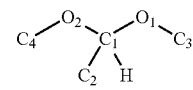

The term "cyclic acetal" refers to an acetal as defined above where $C_3$ and $C_4$, together with the Oxygen atoms to which they are attached, combine thru an alkyl bridge to form a 5- to 10-membered ring, which would be obvious to one of ordinary skill and knowledge in the art. The definition of cyclic acetal includes but is not limited to 2-methyl-[1,3]dioxolane, 2-ethyl-[1,3]dioxane, 2-phenyl-[1,3]dioxane, 2 2-phenyl-hexahydro-pyrano[3,2-d][1,3]dioxine and the like.

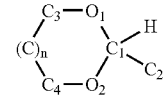

n = 1 to 5

The term "ketal" refers to a molecule that contains a Carbon atom $C_1$ that is directly attached to two substituted Carbon atom ($C_2$ and $C_3$) and two Oxygen atoms ($O_1$ and $O_2$). These Oxygen atoms are in turn attached to other substituted Carbon atoms ($C_4$ and $C_5$), which would be obvious to one of ordinary skill and knowledge in the art. The definition of acetal includes but is not limited to 2,2-dimethoxy-butane, 3,3-diethoxy-pentane and the like.

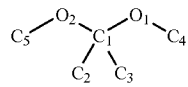

The term "cyclic ketal" refers to a ketal as defined above where $C_4$ and $C_5$, together with the Oxygen atoms to which they are attached, combine thru an alkyl bridge to form a 5- to 10-membered ring, which would be obvious to one of ordinary skill and knowledge in the art. The definition of cyclic acetal includes but is not limited to 2,2,4,5-tetramethyl-[1,3]dioxolane, 2,2-diethyl-[1,3]dioxepane, 2,2-dimethyl-hexahydro-pyrano[3,2-d][1,3]dioxine and the like.

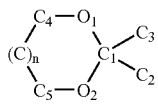

n = 1 to 5

A "C-carboxy" group refers to a —C(=O)OR groups where R is as defined herein.

An "acetyl" group refers to a —C(=O)CH$_3$, group.

A "trihalomethanesulfonyl" group refers to a X$_3$CS(=O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonamido" group refers to a X$_3$CS(=O)$_2$NR— group with X and R as defined herein.

An "O-carbamyl" group refers to a —OC(=O)—NR, group with R as defined herein.

An "N-carbamyl" group refers to a ROC(=O)NH— group, with R as defined herein.

An "O-thiocarbamyl" group refers to a —OC(=S)—NR, group with R as defined herein.

An "N-thiocarbamyl" group refers to an ROC(=S)NH— group, with R as defined herein.

A "C-amido" group refers to a —C(=O)—NR$_2$ group with R as defined herein.

An "N-amido" group refers to a RC(=O)NH— group, with R as defined herein.

The term "perhaloalkyl" refers to an alkyl group where all of the Hydrogen atoms are replaced by halogen atoms.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

Invention compounds according to structural formula 1 include

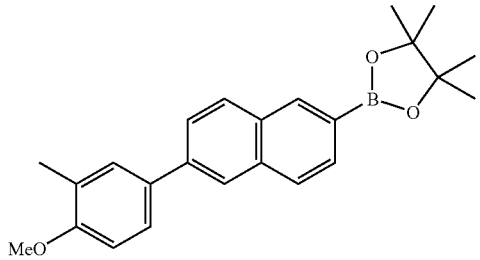

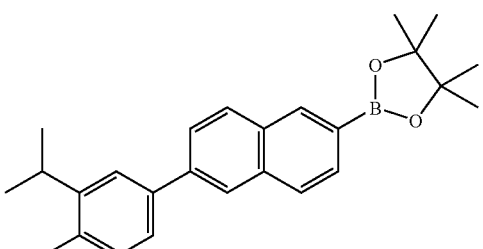

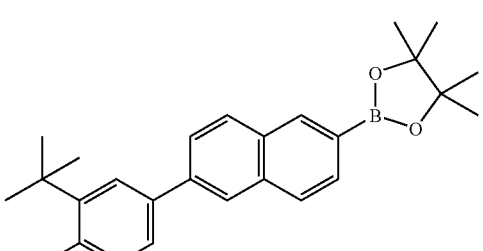

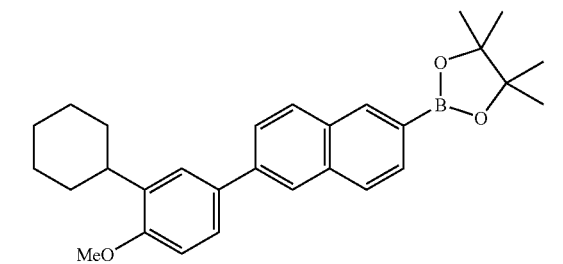
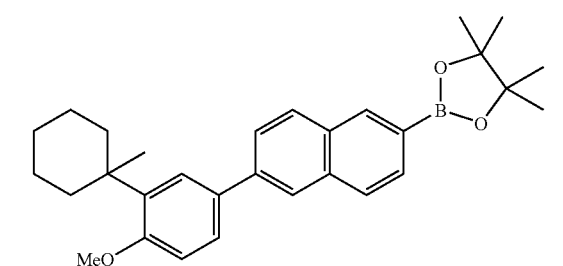
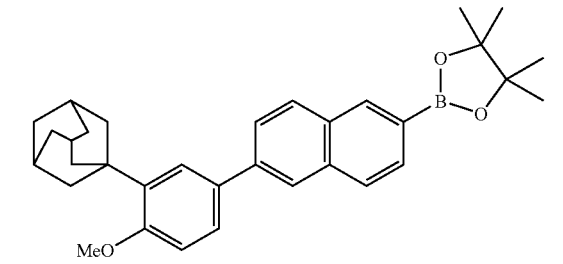
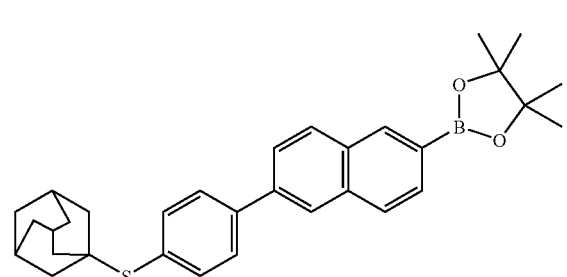
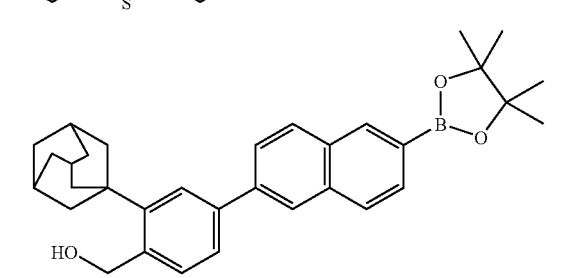
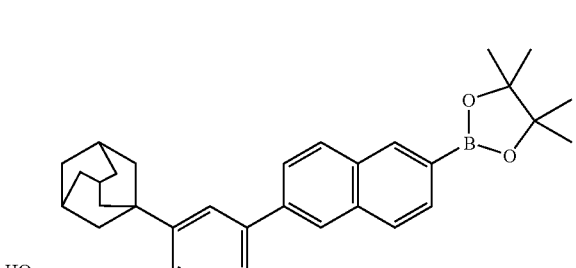
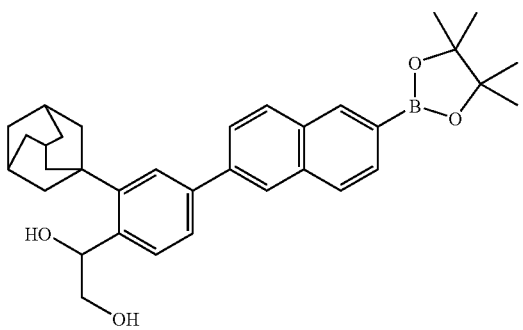
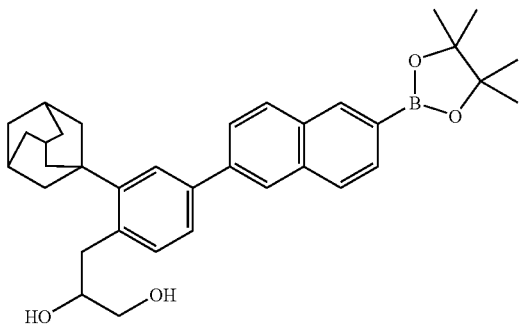
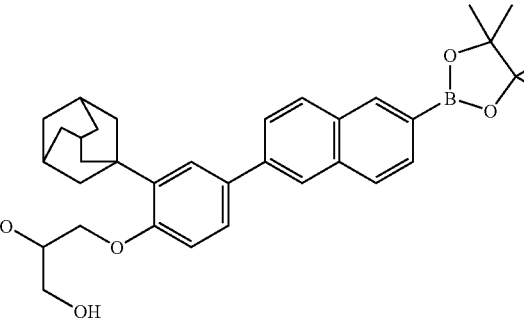
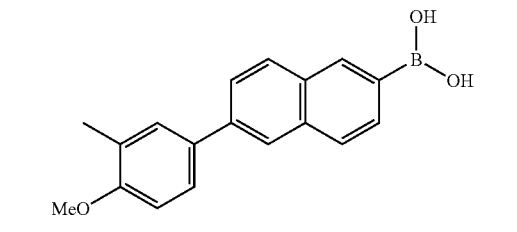
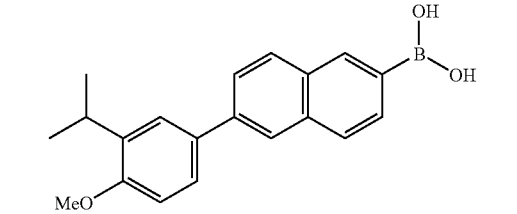
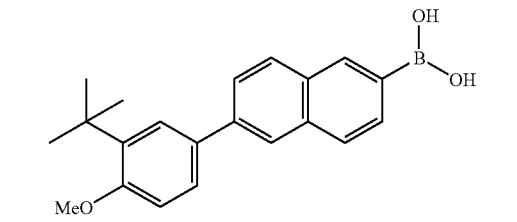

-continued

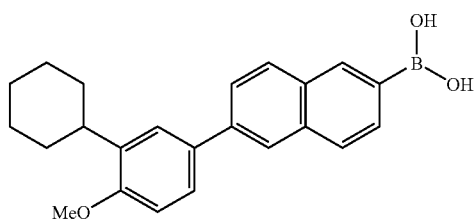
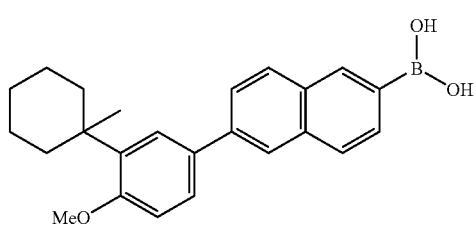
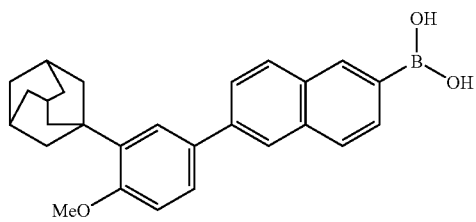
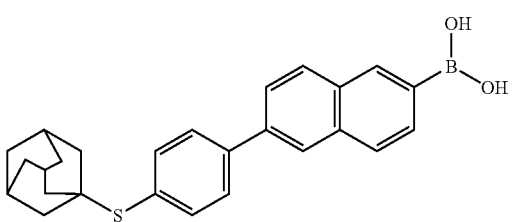
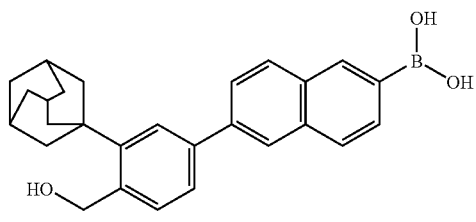
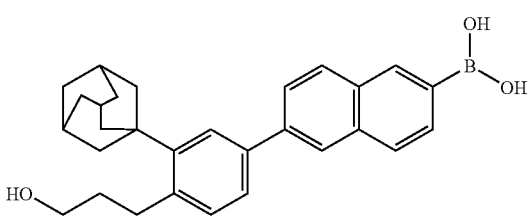
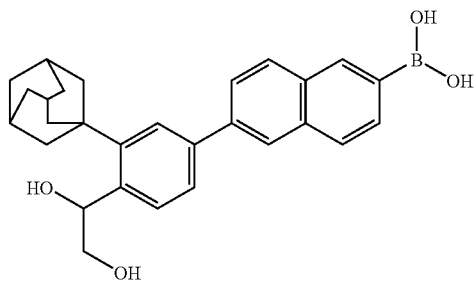

-continued

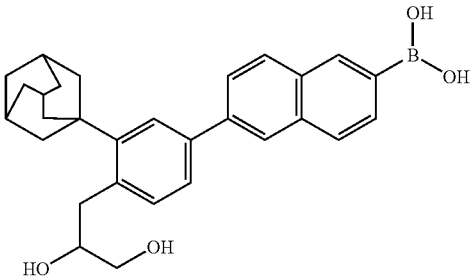
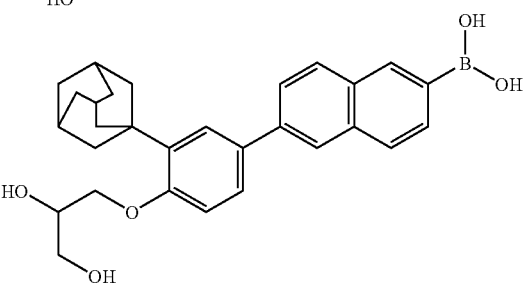

and pharmaceutically acceptable salts, solvates, and prodrugs thereof.

In another embodiment of the invention, there are provided pharmaceutical compositions comprising at least one of the compounds of the invention, as well as pharmaceutically acceptable pro-drugs and salts of such compounds, in a pharmaceutically acceptable vehicle, for enteral, parenteral, topical or ocular administration.

In another embodiment of the invention, there are provided pharmaceutical compositions comprising an effective regulating amount of at least one of the compounds of the invention in combination with a pharmaceutically acceptable carrier, for control of cellular processes, cellular differentiation, cellular proliferation or apoptosis.

In another embodiment of the invention, there are provided pharmaceutical compositions comprising in a pharmaceutically acceptable vehicle suitable for enteral, parenteral, or topical administration, one or more compounds of the invention for treating a mammalian subject wherein said wherein said compound exerts its therapeutic effects via the in vivo modulation of lipid metabolism, lipid homeostasis, hyperlipidemia, skin-related processes, autoimmune diseases, fatty acid metabolism, malignant cell development, premalignant lesions, programmed cell death, endocrinological processes, or AP-1 metabolism.

In another embodiment of the invention, there are provided pharmaceutical compositions comprising at least one of the compounds of the invention, in a pharmaceutically acceptable vehicle, for the treatment of carcinomas. Examples of carcinomas include mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia, and the like.

In another embodiment of the invention, there are provided pharmaceutical compositions comprising at least one the compounds of the invention in combination with other chemotherapeutic agents, in a pharmaceutically acceptable vehicle, for the treatment of carcinomas. Examples of chemotherapeutic agents contemplated for use in the practice of this particular invention include Busulfan, Carboplatin, Cisplatin, Cyclophosphamide, Cytosine arabinoside, Etoposide, 5-Fluorouracil, Melphalan, Methotrexate, Mitoxantrone, Taxol, Irinotican, Gemzar, Interferon, Fareston, Arzoxifene, Evista, Tamoxifen, and the like.

In another embodiment of the invention, there are provided pharmaceutical compositions comprising at least one the compounds of the invention in combination with one or more antiestrogenic agents, in a pharmaceutically acceptable vehicle, for the treatment of mammary carcinoma. Examples of antiestrogenic agents contemplated for use in the practice of this particular invention include Fareston, Arzoxifene, Evista, Tamoxifen, and the like.

In another embodiment of the invention, there are provided cosmeceutical compositions comprising at least one the compounds of the invention, in a cosmetically acceptable vehicle, for dermal indications, acne, and psoriasis.

In another embodiment of the invention, there are provided pharmaceutical compositions comprising at least one the compounds of the invention, in a pharmaceutically acceptable vehicle, for the treatment of diabetes, type I diabetes, type II diabetes, impaired glucose tolerance, insulin resistance, obesity, immune dysfunctions including autoimmunity, diseases with dysfunctions of the coagulation system, allergic diseases, diseases with decreased or increased synthesis or effects of growth hormone, and diseases with decreased or increased synthesis of hormones or cytokines that regulate the release of/or response to growth hormone.

In another embodiment, the present invention provides a process for preparing a compound of formula B. Such a process can be performed, for example, by contacting a compound of formula A with a Boron compound under conditions suitable to form compound of formula B, as set forth below:

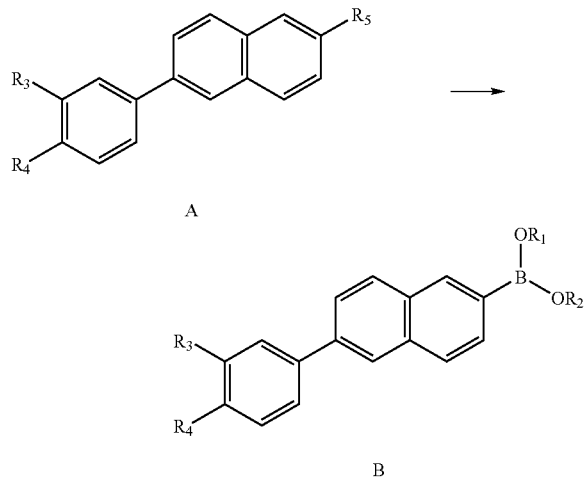

In the scheme shown above, $R_1$, $R_2$, $R_3$, and $R_4$ are as defined above, and $R_5$ is typically halogen and —$OSO_2R_6$ where $R_6$ is typically alkyl, substituted alkyl, aryl and substituted aryl.

Solvents contemplated for use in the practice of this particular invention process are typically ethereal solvents, such as for example, diethyl ether, dioxane, tetrahydrofuran, and the like, aromatic solvents, such as for example, toluene, benzene, and the like, and alcoholic solvents, such as for example, tert-butanol and the like, or any suitable mixtures thereof. The process is typically carried out at a temperature in the range of about 0° C. up to about 500° C., for 0.5 to 240 hours, at a pH in the range of about 7 up to about 12, and at a pressure in the range of about 1 mBar up to about 350 Bar.

Compound A is typically contacted with a Boron containing compound in the presence of a mixture of a palladium catalyst and a base. Palladium catalysts contemplated for use in the practice of this particular invention process include palladium (II) species such as for example palladium (II) acetate, tris(dibenzylideneacetone)-dipalladium, palladium (II) acetylacetonate, palladium (II) bromide, palladium (II) chloride, palladium (II) hexafluoroacetylacetonate, palladium (II) sulfate, palladium (II) trifluoroacetate, dichloro[1,1'-bis(diphenylphosphino)-ferrocene]palladium (II) dichloromethane adduct ($PdCl_2$(dppf)) and the like. Bases contemplated for use in the practice of this particular invention process include potassium acetate, sodium acetate, sodium tert-butoxide, potassium tert-butoxide, cesium carbonate, potassium carbonate, sodium carbonate, potassium phosphate tribasic ($K_3PO_4$), and the like. Boron contain compounds contemplated for use in the practice of this particular invention include optionally substituted [2,2']-bi-[1,3,2]-dioxaborolanes, optionally substituted [2,2']-bi-[1,3,2]-dioxaborinanes, diboron pinacol ester, 2,2'-bi-1,3,2-benzodioxaborole, bis(neopentyl glycolato)diboron, bis(diethyl-L-tartrate glycolato)diboron, bis(diethyl-L-tartrateglycolato) diboron, bis(diethyl-D-tartrate glycolato) diboron, bis (diisopropyl-D-tartrateglycolato)diboron, bis(diisopropyl-L-tartrateglycolato)diboron, bis(n,n,n',n'-tetramethyl-D-tartramideglycolato)diboron, bis(n,n,n',n'-tetramethyl-L-tartramideglycolato)diboron, bis(hexyleneglycolato) diboron, bis(n,n,n',n'-tetramethyl-D-tartaramideglycolato) diboron, bis(n,n,n',n'-tetramethyl-L-tartaramideglycolato) diboron, bis[(−)-pinanediolato]diboron, catecholborane, 4,4,5,5-tetramethyl-1,3,2-dioxaborolane, (+)-pinaneborane, 4,4,6-trimethyl-1,3,2-dioxaborinane, and the like.

In another embodiment, the present invention provides a process for preparing a compound of formula C. Such a process can be performed, for example, by contacting a compound of formula B under conditions suitable to form compound of formula C, as set forth below:

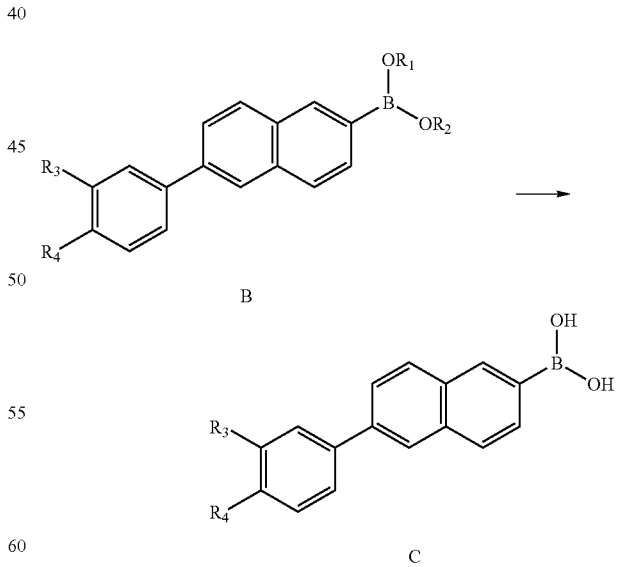

In the scheme shown above, $R_3$, and $R_4$ are as defined above.

Solvents contemplated for use in the practice of this particular invention process are typically diethyl ether, acetonitrile, acetone, dioxane, tetrahydrofuran, toluene, benzene, dichloromethane, water, and the like or any suitable mixtures thereof. The process is typically carried out at a temperature in the range of about 0° C. up to about 500° C., for 0.5 to 240 hours, at a pH in the range of about 0.1 up to about 7, and at a pressure in the range of about 1 mBar up to about 350 Bar.

Compound B is typically contacted with a mixture of an additive and a boron containing compound, where the additive contemplated for use in the practice of this particular invention include an acid, a Lewis acid, trifluoroacetic acid, acetic acid, hydrochloric acid, ammonium acetate, sodium periodate, and the like, and the boron containing compound contemplated for use in the practice of this particular invention include an alkyl boronic acid, aryl boronic acid, heteroaryl boronic acid, polymer supported boronic acid, polystyrene boronic acid, and the like.

Before the present compounds, compositions and methods are disclosed and described, it is to be understood that this invention is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a bicyclic aromatic compound" includes mixtures of bicyclic aromatic compounds, reference to "a pharmaceutical carrier" includes mixtures of two or more such carriers, and the like.

Certain pharmaceutically acceptable salts of the invention are prepared by treating the novel compounds of the invention with an appropriate amount of pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. The reaction is conducted in water, alone or in combination with an inert, water-miscible organic solvent, at a temperature of from about 0° C. to about 100° C., preferably at room temperature. The molar ratio of compounds of structural formula A to base used is chosen to provide the ratio desired for any particular salts. For preparing, for example, the ammonium salts of the starting material, compounds of formula A can be treated with approximately one equivalent of the pharmaceutically acceptable base to yield a neutral salt. When calcium salts are prepared, approximately one-half a molar equivalent of base is used to yield a neutral salt, while for aluminum salts, approximately one-third a molar equivalent of base will be used.

The compounds of the invention according to formula 1, including the pharmacologically acceptable pro-drugs or salts thereof, are useful to elicit, modulate and/or regulate selective gene expression by cellular receptors and provide control over cellular growth, proliferation and differentiation processes regulated by certain hormones or vitamins such as for example all-trans-retinoic acid, 13-cis-retinoic acid, 9-cis-retinoic acid, vitamin D, thyroid hormone and the like. As noted above, the compounds of the invention are thus useful in the treatment of conditions and/or diseases that are regulated by the aforementioned entities. Examples of such conditions include for example cancer, mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia, acne, psoriasis, aging, wrinkling, diabetes, hyperglycemia, bone calcification, thyroid conditions, and the like The compounds of the invention may be conveniently formulated into pharmaceutical compositions composed of one or more of the compounds together with a pharmaceutically acceptable carrier as described in Remington's Pharmaceutical Sciences, latest edition, by E. W. Martin (Mack Publ. Co., Easton Pa.).

The compounds of the invention may be administered orally, parenterally (e.g., intravenously), by intramuscular injection, by intraperitoneal injection, topically, transdermally, or the like, although oral or topical administration is typically preferred. The amount of active compound administered will, of course, be dependent on the subject being treated, the subject's weight, the manner of administration and the judgment of the prescribing physician. The dosage will be in the range of about 2 microgram per kilogram per day to 10 milligram per kilogram per day.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels and the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents and the like.

For solid compositions, conventional non-toxic solid carriers include, for example, pharmaceutical grades of mannitol, lactose, starch, magnesium stearate, sodium saccharin, talc, cellulose, glucose, sucrose, magnesium Carbonate, and the like. Liquid pharmaceutically administrable-compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, fine powders or granules may contain diluting, dispersing, and/or surface active agents, and may be presented in water or in a syrup, in capsules or sachets in the dry state, or in a non-aqueous solution or suspension wherein suspending agents may be included, in tablets wherein binders and lubricants may be included, or in a suspension in water or a syrup. Wherever required, flavoring, preserving, suspending, thickening, or emulsifying agents may also be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, as emulsions, or as sustained release delivery system.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be through nasal sprays, for example, or using suppositories.

For topical administration, the agents are formulated into ointments, creams, salves, powders and gels. In one aspect, the transdermal delivery agent can be DMSO. Transdermal delivery systems can include, such as for example, patches. Topical administration is particularly useful for use of the compound in the treatment of acne or psoriasis.

EXAMPLES

Used herein, the following abbreviations have the following meanings: Me refers to methyl ($CH_3$—), Et refers to ethyl ($CH_3CH_2$—), i-Pr refers to isopropyl (($CH_3)_2CH_2$—), t-Bu or tert-butyl refers to tertiary butyl (($CH_3)_3CH$—), Ph refers to phenyl, Bn refers to benzyl ($PhCH_2$—), Bz refers to benzoyl (PhCO—), MOM refers to methoxymethyl, Ac refers to acetyl, TMS refers to trimethylsilyl, TBS refers to ter-butyldimethylsilyl, Ms refers to methanesulfonyl ($CH_3SO_2$—), Ts refers to p-toluenesulfonyl (p—$CH_3PhSO_2$—), Tf refers to trifluoromethanesulfonyl ($CF_3SO_2$—), TfO refers to trifluoromethanesulfonate ($CF_3SO_3$—), DMF refers to N,N-dimethylformamide, DCM refers to dichloromethane ($CH_2Cl_2$), THF refers to tetrahydrofuran, EtOAc refers to ethyl acetate, $Et_2O$ refers to diethyl ether, MeCN refers to acetonitrile ($CH_3CN$), NMP refers to 1-N-methyl-2-pyrrolidinone, DMA refers to N,N-dimethylacetamide, DMSO refers to dimethylsulfoxide, DCC refers to 1,3-dicyclohexyldicarbodiimide, EDCI refers to 1-(3-dimethylaminopropyl)-3-ethylcarbodiimide, Boc refers to tert-butylcarbonyl, Fmoc refers to 9-fluorenylmethoxycarbonyl, TBAF refers to tetrabutylammonium fluoride, TBAI refers to tetrabutylammonium iodide, TMEDA refers to N,N,N,N-tetramethylethylene diamine, Dess-Martin periodinane or Dess Martin reagent refers to 1,1,1-triacetoxy-1,1-dihydro-1,2-benziodoxol-3(1H)-one, DMAP refers to 4-N,N-dimethylaminopyridine, (i-Pr)$_2$NEt or DIEA or Hunig's base refers to N,N-diethylisopropylamine, DBU refers to 1,8-Diazabicyclo[5.4.0]undec-7-ene, (DHQ)$_2$AQN refers to dihydroquinine anthraquinone-1,4-diyl diether, (DHQ)$_2$PHAL refers to dihydroquinine phthalazine-1,4-diyl diether, (DHQ)$_2$PYR refers to dihydroquinine 2,5-diphenyl-4,6-pyrimidinediyl diether, (DHQD)$_2$AQN refers to dihydroquinidine anthraquinone-1,4-diyl diether, (DHQD)$_2$PHAL refers to dihydroquinidine phthalazine-1,4-diyl diether, (DHQD)$_2$PYR refers to dihydroquinidine 2,5-diphenyl-4,6-pyrimidinediyl diether, LDA refers to lithium diisopropylamide, LiTMP refers to lithium 2,2,6,6-tetramethylpiperidinamide, n-BuLi refers to n-butyllithium, t-BuLi refers to tert-butyl lithium, IBA refers to 1-hydroxy-1,2-benziodoxol-3(1H)-one 1-oxide, $OsO_4$ refers to osmium tetroxide, m-CPBA refers to meta-chloroperbenzoic acid, DMD refers to dimethyl dioxirane, PDC refers to pyridinium dichromate, NMO refers to N-methyl morpholine-N-oxide, NaHMDS refers to sodium hexamethyldisilazide, LiHMDS refers to lithium hexamethyldisilazide, HMPA refers to hexamethylphosphoramide, TMSCl refers to trimethylsilyl chloride, TMSCN refers to trimethylsilyl cyanide, TBSCl refers to tert-butyldimethylsilyl chloride, TFA refers to trifluoroacetic acid, TFAA refers to trifluoroacetic anhydride, AcOH refers to acetic acid, $Ac_2O$ refers to acetic anhydride, AcCl refers to acetyl chloride, TsOH refers to p-toluenesulfonic acid, TsCl refers to p-toluenesulfonyl chloride, MBHA refers to 4-methylbenzhydrylamine, BHA refers to benzhydrylamine, $ZnCl_2$ refers to zinc (II) dichloride, $BF_3$ refers to boron trifluoride, Y(OTf)$_2$ refers to yttrium (III) trifluoromethanesulfonate, Cu($BF_4$)$_2$ refers to copper (II) tetrafluoroborate, LAH refers to lithium aluminum hydride (Li-Al$H_4$), NaHCO$_3$ refers to sodium biCarbonate, $K_2CO_3$ refers to potassium Carbonate, NaOH refers to sodium hydroxide, KOH refers to potassium hydroxide, LiOH refers to lithium hydroxide, HCl refers to hydrochloric acid, $H_2SO_4$ refers to sulfuric acid, $MgSO_4$ refers to magnesium sulfate, and $Na_2SO_4$ refers to sodium sulfate. 1H NMR refers to proton nuclear magnetic resonance, 13C NMR refers to Carbon 13 nuclear magnetic resonance, NOE refers to nuclear overhauser effect, NOESY refers to nuclear overhauser and exchange spectroscopy, COSY refers to homonuclear correlation spectroscopy, HMQC refers to proton detected heteronuclear multiplet-quantum coherence, HMBC refers to heteronuclear multiple-bond connectivity, s refers to singlet, br s refers to broad singlet, d refers to doublet, br d refers to broad doublet, t refers to triplet, q refers to quartet, dd refers to double doublet, m refers to multiplet, ppm refers to parts per million, IR refers to infrared spectrometry, MS refers to mass spectrometry, HRMS refers to high resolution mass spectrometry, EI refers to electron impact, FAB refers to fast atom bombardment, CI refers to chemical ionization, HPLC refers to high pressure liquid chromatography, TLC refer to thin layer chromatography, R$_f$ refers to, R$_t$ refers to retention time, GC refers to gas chromatography, min is minutes, h is hours, rt or RT is room temperature, g is grams, mg is milligrams, L is liters, mL is milliliters, mol is moles and mmol is millimoles.

For all of the following examples, standard work-up and purification methods can be utilized and will be obvious to those skilled in the art. Synthetic methodologies that make up the invention are shown in Schemes 1-2. These Schemes are intended to describe the applicable chemistry through the use of specific examples and are not indicative of the scope of the invention.

Example 1

1-(5-Bromo-2-methoxyphenyl)-adamantane

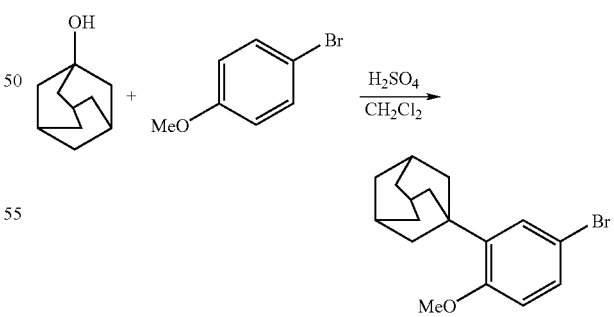

Reagent grade concentrated $H_2SO_4$ (11 mL) was added dropwise to a solution of 1-adamantol (30.25 g, 200 mmol) and 4-bromoanisole (37.21 g, 200 mmol) in 130 mL of $CH_2Cl_2$. The light pink solution was stirred at ambient temperature for 20 hours. The solvent was decanted, water (100 mL) and hexane (100 mL) were added and the solid was filtered and washed with hexane and dried to give 31 g of the product as a white powder. The supernatant was diluted with hexane, washed with water and brine, dried over MgSO₄ and filtered thru a silica gel pad. The solvent was removed and the solid was recrystallized from hexane to yield 17 g of the product as a white powder.

Yield: 48 g (75%); white solid; Rf=0.9 in 25% EtOAc-hexane. 1H NMR (CDCl₃, 300 MHz) ☐ 1.78 (s, 6H), 2.08 (s, 9H), 3.81 (s, 3H), 6.72 (d, 1H), 7.24 (dd, 1H), 7.28 (m, 1H).

Example 2

1-(5-Boronic acid-2-methoxyphenyl)-adamantane

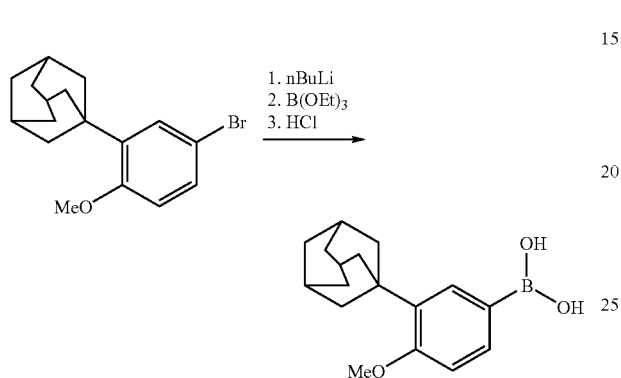

To a solution of 1-(5-bromo-2-methoxyphenyl)-adamantane (4 g, 12.5 mmol) in 40 mL of THF was added a 2.5M solution of n-BuLi in hexane (5 mL, 12.5 mmol) at −78° C., under nitrogen. The mixture was stirred for 5 minutes at −78° C., triethylborate (1.88 g, 12.9 mmol) was added and the mixture was stirred for an additional 30 minutes at −78° C. The reaction was allowed to slowly warm to room temperature and was quenched by addition of 1N HCl (30 mL). The mixture was diluted with Et₂O, washed with water and brine, dried over Na₂SO₄, filtered thru a pad of silica gel and the solvent was removed to yield the crude product which was recrystallized from chloroform.

Yield: 0.45 g (12%); white solid; 1H NMR (CDCl₃-MeOD 10:1, 300 MHz) ☐ 1.74 (s, 6H), 2.08 (m, 9H), 2.9 (s, 2H), 3.81 (s, 3H), 6.82 (d, 1, 7.52 (m, 2H)

Example 3

2-tert-Butyl-dimethylsilanoxy-6-bromo-naphthalene

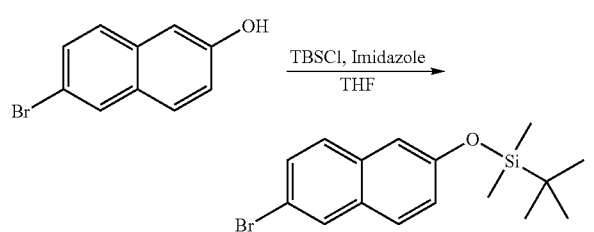

To a solution of 6-bromo-2-napthol (1.12 g, 5 mmol) in anhydrous THF (15 mL) was added imidazole (0.476 g, 7 mmol) followed by TBSCl (1.05 g, 7 mmol) at room temperature under nitrogen atmosphere. The reaction mixture was stirred at room temperature for 40 h and was diluted with ether, washed with brine and dried over anhydrous Mg2SO4.

The solvent was removed to yield the crude product, which was recrystallized from methanol. Yield: 1.36 g (80%), white crystals. 1H-NMR (CDCl3) ☐ 0.08 (s, 6H), 1.06 (s, 9H), 7.08 (dd, 1H), 7.15 (s, 1H), 7.47 (dd, 1H), 7.56 (d, 1H), 7.64 (d, 1H), 7.92 (s, 1H).

Example 4

2-tert-Butyl-dimethylsilanoxy-6-boronic acid-naphthalene

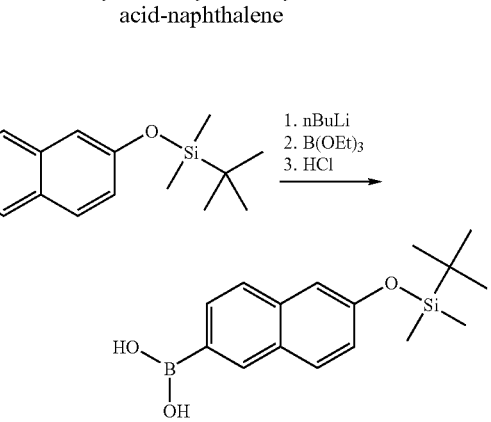

Prepared according to example 2, starting with 30 g of the bromide. The crude product was recrystallized from hexane.

Yield: 24 g (89%), white solid. 1H-NMR (CDCl3) ☐ 0.3 (s, 6H), 1.05 (s, 9H), 7.16 (dd, 1H), 7.26 (m, 1H), 7.82 (d, 1H), 7.98 (d, 1H), 8.24 (dd, 1H), 8.8 (s, 1H).

Example 5

2-tert-Butyl-dimethylsiloxy 6-(3-adamantan-1-yl-4-methoxyphenyl)naphthalene

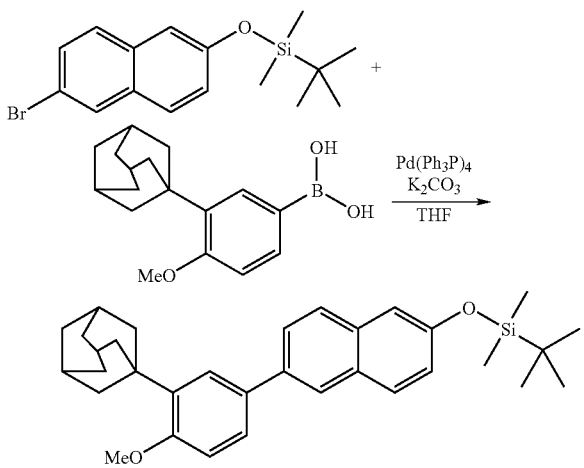

1-(5-Boronic acid-2-methoxyphenyl)-adamantane (429 mg, 1.5 mmol), 2-tert-butyl-dimethylsilanoxy-6-bromo-naphthalene (337 mg, 1 mmol) and palladium tetrakis(triphenylphosphine) (58 mg, 0.05 mmol) were placed in a Schlenk flask and the vessel was flushed with nitrogen. Degassed THF (3 mL) and degassed 1 M aqueous K₂CO₃ (2.5 mL) were added to the reaction flask and the mixture was placed in a 70° C. bath and stirred under nitrogen for 3.5 hours. The reaction was cooled to room temperature and the layers were separated. The organic layer was dried over Na$_2$SO$_4$ and filtered thru a short pad of silica gel. The solvent was removed to yield the product.

Yield: 0.45 g (90%); white solid; R$_f$=0.7 in 25% EtOAc-hexane. $^1$H NMR (CDCl$_3$, 300 MHz) □ 0.3 (s, 6H), 1.05 (s, 9H), 1.72 (s, 6H), 2.2 (s, 3H), 2.4 (s, 6H), 3.81 (s, 3H), 6.98 (d, 1H), 7.09 (dd, 1H), 7.2 (d, 1H), 7.5 (dd, 1H), 7.56 (d, 1H), 7.66 (dd, 1H), 7.75 (m, 2H), 7.9 (d, 1H)

Example 6

2-tert-Butyl-dimethylsiloxy 6-(3-adamantan-1-yl-4-methoxyphenyl)naphthalene

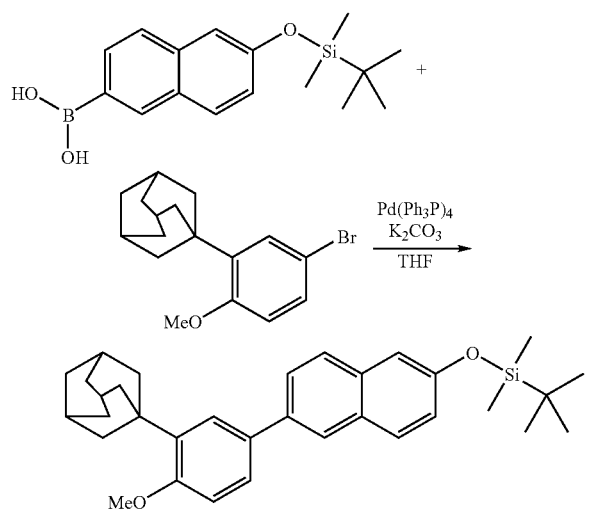

Prepared according to example 5, starting with 5.8 g of the bromide. The crude product was filtered thru a short pad of silica gel.

Yield: 7.7 g (85%); white solid; R$_f$=0.7 in 25% EtOAc-hexane.

Example 7

Toluene-4-sulfonic acid 6-(3-adamantan-1-yl-4-methoxyphenyl)naphthalen-2-yl ester

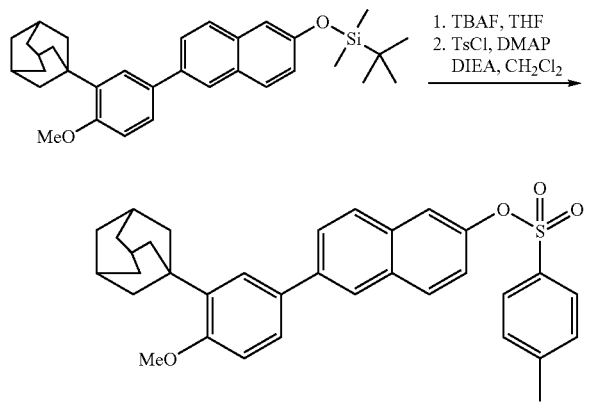

To a solution of 2-tert-butyl-dimethylsiloxy-6-(3-adamantan-1-yl-4-methoxyphenyl)-naphthalene (14 g, 28 mmol) in THF (160 ml) was added TBAF (28 ml, 28 mmol) and the reaction stirred at RT for 5 min. The reaction mixture was diluted with EtOAc and washed with 1N HCl, brine, and dried over Na$_2$SO$_4$. The crude product was concentrated in vacuo and the residue was dissolved in DCM (200 ml). DMAP (0.2 equiv), DIEA (1.2 equiv) and toluene-4-sulfonyl chloride (1 equiv) were added and the reaction was stirred at RT for 30 minutes. The solvent was removed, the residue was dissolved in EtOAc, washed with 1N HCl, brine, and dried over Na$_2$SO$_4$. The solvent was removed and the crude product was recrystallized from acetonitrile.

Yield: 12.2 g (81%); Rf=0.65 in 25% EtOAc-hexane. 1H NMR (CDCl$_3$, 300 MHz) □ 1.81 (s, 6H), 2.11 (s, 3H), 2.19 (s, 6H), 3.91 (s, 3H), 6.98 (d, 1H), 7.09 (dd, 1H), 7.3 (m, 2H), 7.52 (m, 3H), 7.75 (m, 5H), 7.94 (s, 1H).

Example 8

Trifluoromethanesulfonic acid 6-(3-adamantan-1-yl-4-methoxy-phenyl)naphthalen-2-yl ester

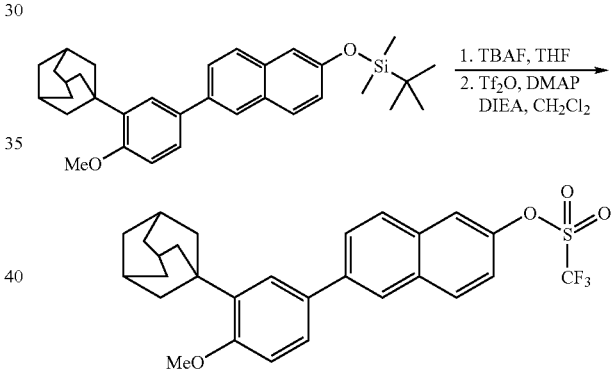

The tert-butyl-dimethylsiloxy protecting group is removed as in example 7. A solution of 6-[3-(1-adamandyl)-4-methoxyphenyl]-naphthalen-2-ol (19 g, 48.2 mmol), N,N-diisopropylethyl amine (6.2 g, 48.2 mmol) and DMAP (5.6 g, 48.2 mmol) in anhydrous CH$_2$Cl$_2$ (350 mL) was cooled to −78° C. Trifluoromethanesulfonic anhydride (15 g, 531 mmol) was added dropwise at −78° C. and the reaction was stirred for an hour, brought to room temperature, diluted with water (500 mL), extracted with CH$_2$Cl$_2$ (500×2 mL), washed with water (300 mL), brine solution (100 mL) and dried (Na$_2$SO$_4$). The solvent was removed and the residue was recrystallized from hexane-ethanol (5:1, 100 mg/mL) to give the product as a white crystalline solid.

Yield: 18.8 g (77%). $^1$H-NMR (CDCl$_3$) δ ppm: 1.8 (br s, 6H), 2.12 (br s, 3H), 2.2 (s, 6H), 3.9 (s, 3H); 7.0 (d, 1H); 7.4 (d of d, 1H); 7.52 (d, 1H); 7.6 (s, 1H); 7.78-8.02 (m, 5H). $^{13}$C-NMR (CDCl$_3$) δ ppm: 29.50, 37.50, 37.59, 40.97, 55.50, 112.36, 119.24, 120.04, 121.18, 125.05, 125.90, 126.12, 127.67, 128.56, 130.84, 132.21, 132.50, 132.98, 139.25, 140.66, 146.98, 159.07.

Example 9

2-[6-(3-(1-Adamandyl)-4-methoxyphenyl)-naphthalen-2-yl]-4,4,5,5-tetramethyl[1,3,2]dioxaborolane

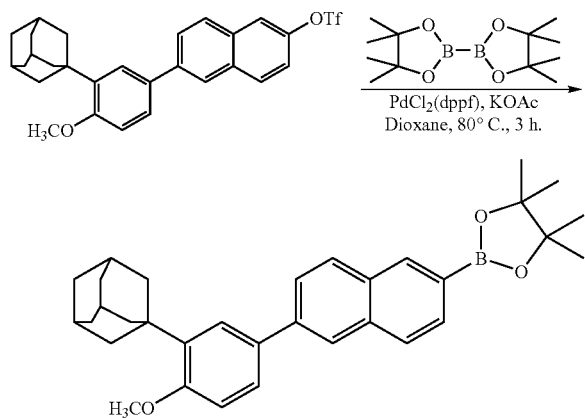

A two neck round bottomed flask was charged with trifluoromethanesulfonic acid 6-[3-(1-adamandyl)-4-methoxyphenyl]-naphthalen-2-yl ester (4.96 g, 9.6 mmol), dichloro[1,1'-bis(diphenylphosphino)ferrocene]palladium (II) dichloromethane adduct (PdCl$_2$(dppf), 282 mg, 0.385 mmol), diboron pinacol ester (2.93 g, 11.5 mmol), and potassium acetate (2.85 g, 28.5 mmol). The apparatus was flushed with dry nitrogen and the solid mixture was taken up in anhydrous 1,4-dioxane (60 mL); the reaction mixture was placed in a pre-heated oil bath at 80° C. for 3 h. The reaction was diluted with EtOAc (150 mL), washed with water (100 mL), brine (20 mL) and dried over anhydrous Na$_2$SO$_4$. The solvent was removed and the residue was purified by on silica gel using 20% EtOAc-hexane to give the product as a white solid. Yield: 4.6 g (97%). $^1$H-NMR (CDCl$_3$) δ ppm: 1.4 (s, 12H); 1.8 (br s, 6H), 2.18 (br s, 3H), 2.22 (s, 6H), 3.9 (s, 3H); 7.0 (d, 1H); 7.52 (d of d, 1H); 7.6 (s, 1H); 7.72 (d of d, 1H); 7.8-8.0 (m, 4H); 8.38 (s, 1H).

Example 10

6-[-3-(1-Adamandyl)-4-methoxyphenyl)-2-naphthoboronic acid

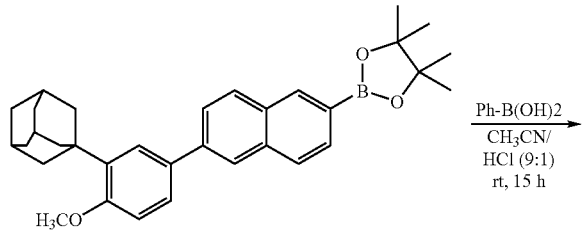

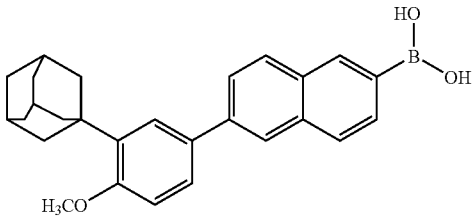

A mixture of 2-[6-(3-(1-adamandyl)-4-methoxyphenyl)-naphthalen-2-yl]-4,4,5,5-tetramethyl[1,3,2]dioxaborolane (4.0 g, 8 mmol) and phenylboronic acid (4.8 g, 40 mmol) in 70 mL of 9:1 THF-1N HCl was stirred at room temperature for 15 h. The solvent was removed under vacuum and the residue was diluted with water (60 mL) and the pH was adjusted to 10 with 1N NaOH. The aqueous solution was extracted with EtOAc (50×3 mL), and the organic layer was washed with water (100 mL), brine (20 mL) and dried (Na$_2$SO$_4$). The solvent was removed and the crude residue was purified by flash column chromatography using 10% EtOAc-DCM to give the product as a white powder.

Yield: 2 g (60%). $^1$H-NMR (CDCl$_3$-CD$_3$OD) δ ppm: 1.8 (br s, 6H), 2.1 (br s, 3H), 2.2 (s, 6H), 3.88 (s, 3H); 6.98 (d, 1H); 7.5 (d of d, 1H); 7.56 (s, 1H); 7.6-7.78 (m, 2H); 7.8-8.0 (m, 3H); 8.38 (2s, 1H). Mass: 447 [M+Cl$^-$]$^-$.

Example 11

Topical Gel

Combination of the active principle with propylene glycol, carbomer 940, poloxamer 182, edetate disodium, methylparaben, sodium hydroxide, hydrochloric acid and purified water. The amount of the active principle may be 0.001 to 10 weight percent based on the total weight of said composition. An example of an active principle is 6-[-3-(1-Adamandyl)-4-methoxyphenyl)-2-naphthoboronic acid.

Example 12

Topical Gel

Combination of the active principle with butylated hydroxytoluene, hydroxypropyl cellulose, polyolprepolymer-2, and ethanol (denatured with tert-butyl alcohol and brucine sulfate) 83% w/w. The amount of the active principle may be 0.001 to 10 weight percent based on the total weight of said composition. An example of an active principle is 6-[-3-(1-Adamandyl)-4-methoxyphenyl)-2-naphthoboronic acid.

Example 13

Topical Gel

Combination of the active principle with ascorbic acid, butylated hydroxyanisole, butylated hydroxytoluene, carbomer 934P, edetate disodium, hexylene glycol, purified water, poloxamer 407, polyethylene glycol 400, polysorbate 40, and tromethamine. The amount of the active principle may be 0.001 to 10 weight percent based on the total weight of said composition. An example of an active principle is 6-[-3-(1-Adamandyl)-4-methoxyphenyl)-2-naphthoboronic acid.

Example 14

Topical Cream

Combination of the active principle with stearic acid, polyolprepolymer-2, isopropyl myristate, polyoxy 40 stearate, propylene glycol, stearyl alcohol, xanthan gum, sorbic acid, butylated hydroxytoluene, and purified water. The amount of the active principle may be 0.001 to 10 weight percent based on the total weight of said composition. An example of an active principle is 6-[-3-(1-Adamandyl)-4-methoxyphenyl)-2-naphthoboronic acid.

Example 15

Topical Cream

Combination of the active principle with Cetearyl octanoate, glycerin, glyceryl stearate, cetearyl alcohol, cetyl palmitate, cocoglycerides, PEG-5 glyceryl stearate, propylene glycol, and purified water. The amount of the active principle may be 0.001 to 10 weight percent based on the total weight of said composition. An example of an active principle is 6-[-3-(1-Adamandyl)-4-methoxyphenyl)-2-naphthoboronic acid.

Example 16

Topical Cream

Combination of the active principle with carbomer 934P, cyclomethicone, edetate disodium, glycerin, methyl glucose sesquistearate, methyl paraben, PEG-20 methyl glucose sesquistearate, phenoxyethanol, propylparaben, purified water, squalene, and trolamine. The amount of the active principle may be 0.001 to 10 weight percent based on the total weight of said composition. An example of an active principle is 6-[-3-(1-Adamandyl)-4-methoxyphenyl)-2-naphthoboronic acid.

Example 17

Co-Transfection Assay

The following assay is a measure of the in-vitro binding affinity of the given compound with human RAR-β in COS-7 cells. Binding of the compound to RAR-β will induce transcription of luciferase within the cells. This level of transcription can be quantified based on the amount of luminescence emitted after incubation of the cell lysate with luciferin.

COS-7 cells were cultured in Dulbecco Modified Eagle's Medium (DMEM) with 4 mM L-glutamine, 4.5 g/L glucose 1.5 g/L sodium bicarbonate and supplemented with 10% fetal bovine serum. Cells were transfected using the calcium phosphate:DNA co-precipitation method. A 10-cm plate of cells was transfected with 5 μg of luciferase reporter construct, 5 μg of expression vector for β-galactosidase, 1 μg of expression vector for RAR-β, and pUC19 as carrier, to a total of 20 μg.

β-galactosidase (5 μg) was included in each transfection to monitor transfection efficiency. Cells were incubated 6 hours at 37° C. in a $CO_2$ incubator. The cells were re-suspended in fresh media containing 10% serum (96-well plate, 15000 cells per well) with or without compound (in 0.5% DMSO) and the plates were incubated at 37° C. in a $CO_2$ incubator. Lysis buffer (1×) was added to cover the cells and the plates were incubated at ambient temperature for 15 min. Luciferase and β-galactosidase assays were performed 36 hours post-transfection, and the normalized luciferase response was determined as relative light units divided by β-galactosidase activity. Composition of 5× lysis buffer is 125 mM. Tris (pH 7.8) with $H_3PO_4$ 10 mM trans-1,2 diaminocyclohexane-N,N, N',N'-tetraaceticacid (CDTA), 10 mM dithiothereitol (DTT), 50% glycerol, 5% triton X-100.

The table below shows the fold induction of luciferase in COS 7 cells. ATRA stands for all-trans-retinoic acid.

|  | μM | Fold Induction |
| --- | --- | --- |
| Example 9 | 40 | 6 |
| Example 9 | 3 | 2 |
| Example 10 | 10 | 3.6 |
| Example 10 | 3 | 2.1 |
| ATRA | 0.1 | 19.1 |
| ATRA | 0.03 | 13.7 |
| ATRA | 0.001 | 9.3 |

The compounds of this invention are novel therapeutic agents for the treatment of cancer, metabolic diseases and skin disorders in mammalian subjects. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

What is claimed is:

1. Compounds having the structural formula 1:

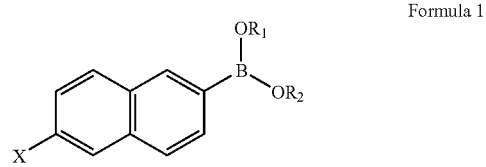

Formula 1 wherein X has structural formula 2:

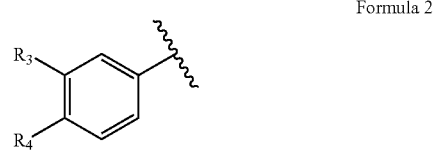

Formula 2

$R_1$ and $R_2$ are selected from the group consisting of hydrogen and alkyl; or $R_1$ and $R_2$ may be linked together to form

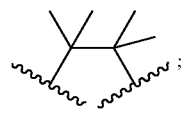

;

$R_3$ is selected from the group consisting of hydrogen, alkyl, adamantyl; and

R4 is selected from the group consisting of hydrogen, alkyl, alkyloxy, and alkylthio; and pharmaceutically acceptable salts thereof.

2. A pharmaceutical composition comprising a pharmaceutically acceptable vehicle suitable for enteral, parenteral, topical or ocular administration and an effective amount of an active principle composed of at least one compound of claim 1 or a pharmaceutically acceptable salt thereof.

3. A pharmaceutical composition according to claim 2 wherein said active principle is present in an amount ranging from 0.0001 to about 10 weight percent based on the total weight of said composition.

4. A pharmaceutical composition comprising at least one compound according to claim 1.

5. A compound selected from the group consisting of

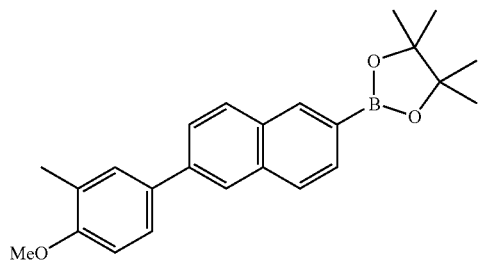

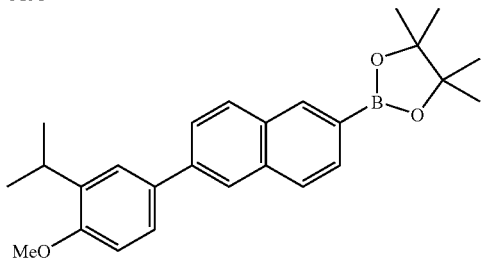

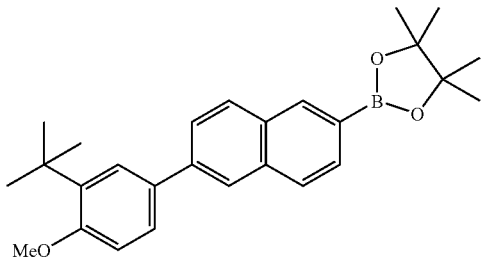

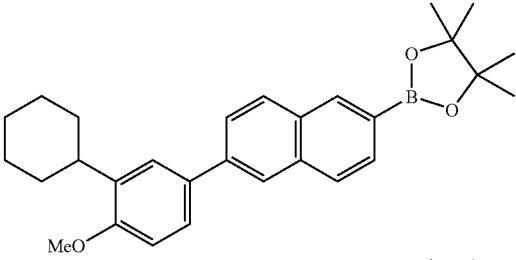

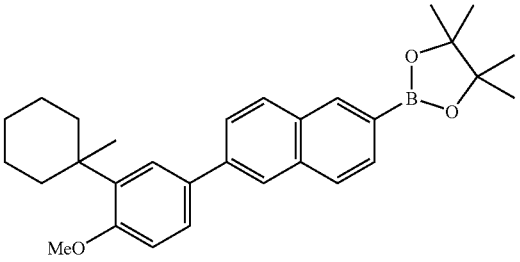

-continued

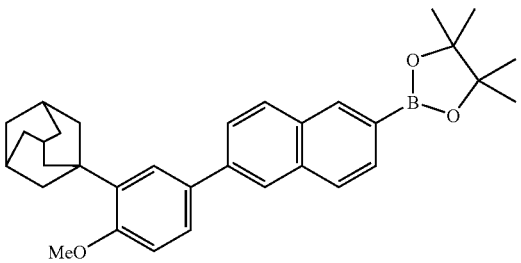

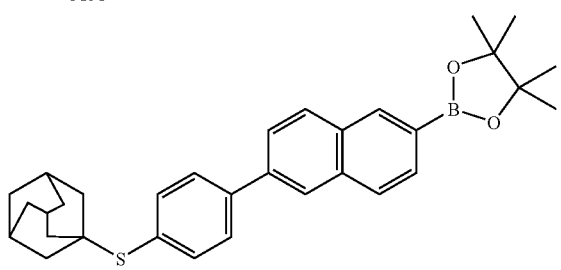

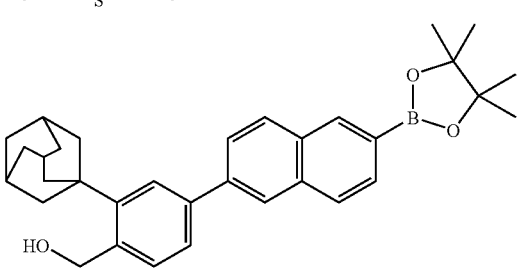

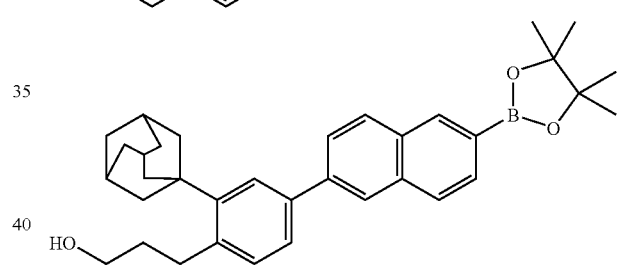

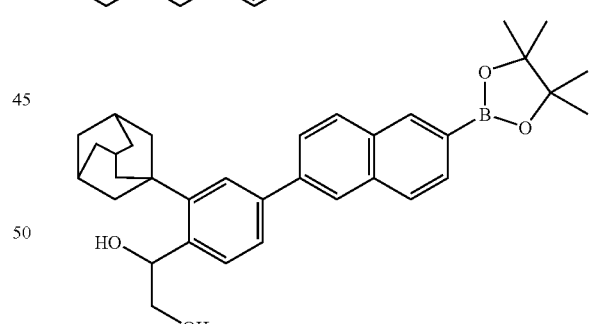

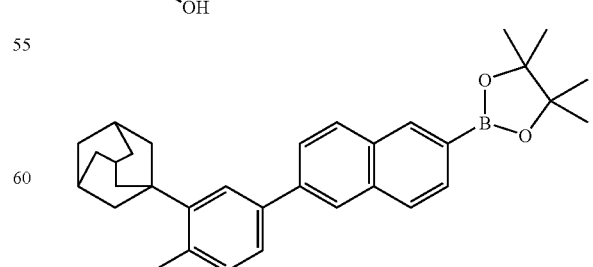

-continued
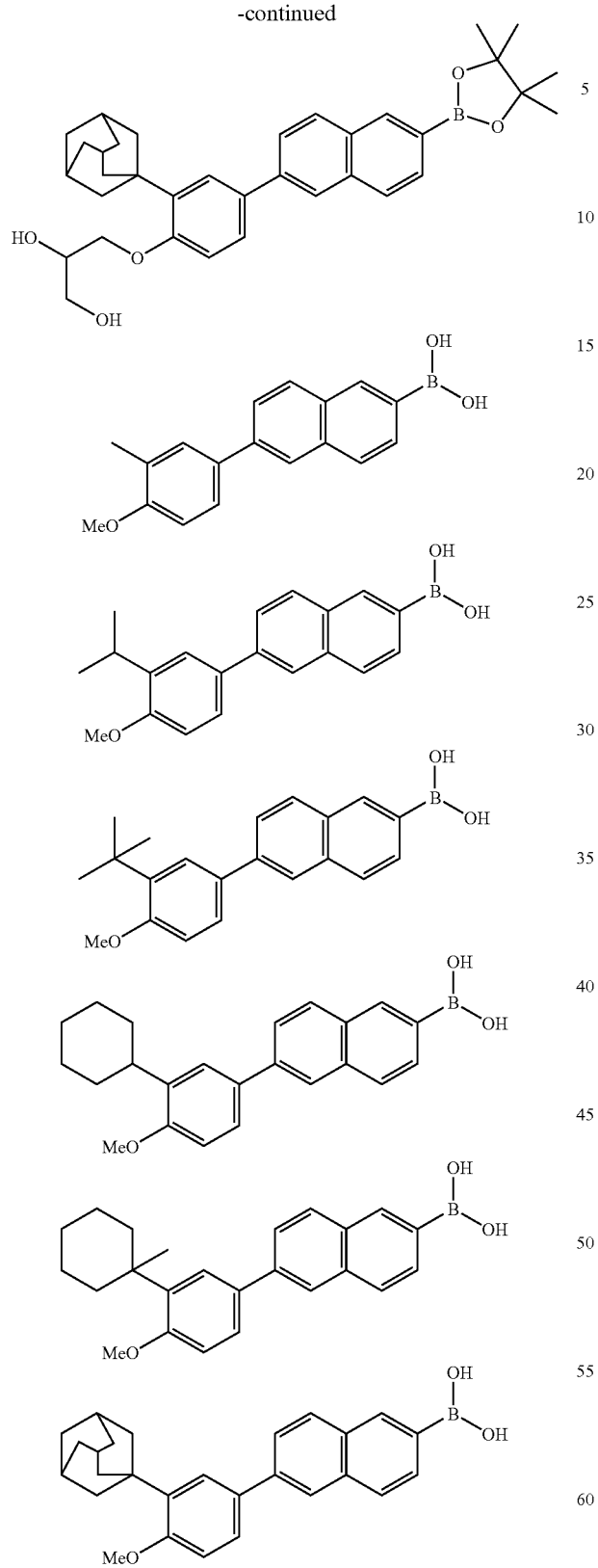
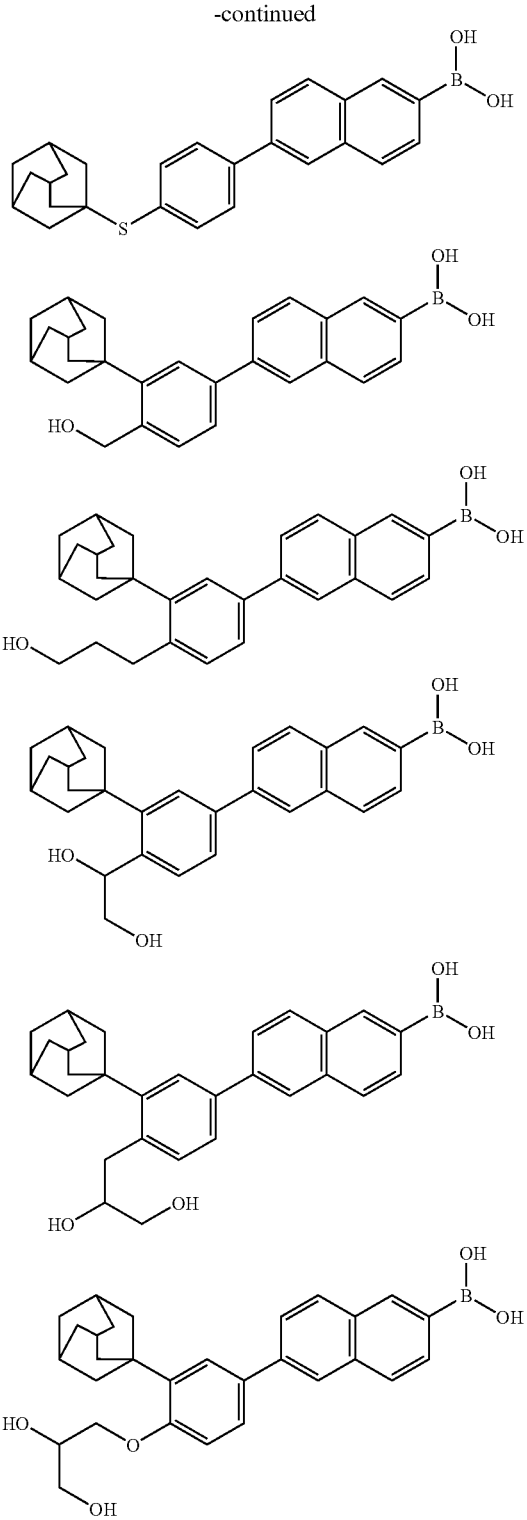
and pharmaceutically acceptable salts thereof.
* * * * *